United States Patent
Amancha et al.

(10) Patent No.: US 9,918,981 B2
(45) Date of Patent: *Mar. 20, 2018

(54) LIQUID BUPRENORPHINE FORMULATIONS

(71) Applicant: Insys Development Company, Inc., Chandler, AZ (US)

(72) Inventors: Kiran P. Amancha, Chandler, AZ (US); Chandeshwari S. Chilampalli, Phoenix, AZ (US); Venkat R. Goskonda, Phoenix, AZ (US)

(73) Assignee: INSYS DEVELOPMENT COMPANY, INC., Chandler, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/336,547

(22) Filed: Oct. 27, 2016

(65) Prior Publication Data

US 2017/0042884 A1    Feb. 16, 2017

Related U.S. Application Data

(63) Continuation-in-part of application No. 14/923,630, filed on Oct. 27, 2015, now Pat. No. 9,839,611, which is a continuation-in-part of application No. 14/469,063, filed on Aug. 26, 2014, now Pat. No. 9,216,175.

(60) Provisional application No. 61/875,837, filed on Sep. 10, 2013.

(51) Int. Cl.
| | |
|---|---|
| A61K 31/485 | (2006.01) |
| A61K 9/00 | (2006.01) |
| A61K 47/10 | (2017.01) |
| A61K 31/4748 | (2006.01) |
| A61K 47/22 | (2006.01) |
| A61K 47/18 | (2017.01) |
| A61K 47/02 | (2006.01) |
| A61K 47/40 | (2006.01) |

(52) U.S. Cl.
CPC ............ *A61K 31/485* (2013.01); *A61K 9/006* (2013.01); *A61K 31/4748* (2013.01); *A61K 47/10* (2013.01); *A61K 47/02* (2013.01); *A61K 47/183* (2013.01); *A61K 47/22* (2013.01); *A61K 47/40* (2013.01)

(58) Field of Classification Search
CPC ....... A61K 31/485; A61K 47/10; A61K 9/006
See application file for complete search history.

(56) References Cited

U.S. PATENT DOCUMENTS

| | | |
|---|---|---|
| 6,365,596 B1 | 4/2002 | Valenti |
| 6,413,496 B1 | 7/2002 | Goodman et al. |
| 7,501,113 B2 | 3/2009 | Blondino et al. |
| 7,666,876 B2 | 2/2010 | Birch et al. |
| 8,211,946 B2 | 7/2012 | Whittle |
| 8,475,832 B2 | 7/2013 | Myers et al. |
| 2003/0003113 A1 | 1/2003 | Lewandowski |
| 2003/0166624 A1 | 9/2003 | Gale et al. |
| 2003/0190290 A1 | 10/2003 | Ross |
| 2004/0192714 A1 | 9/2004 | Boer et al. |
| 2007/0148097 A1 | 6/2007 | Finn et al. |
| 2009/0117054 A1 | 5/2009 | Crooks et al. |
| 2009/0176834 A1 | 7/2009 | Kottayil et al. |
| 2009/0270438 A1 | 10/2009 | Booles et al. |
| 2010/0015183 A1 | 1/2010 | Finn et al. |
| 2010/0087470 A1 | 4/2010 | Oksche et al. |
| 2010/0120812 A1 | 5/2010 | Chapleo et al. |
| 2010/0233257 A1 | 9/2010 | Herry et al. |
| 2011/0189259 A1 | 8/2011 | Vasisht et al. |
| 2011/0245288 A1 | 10/2011 | Stinchcomb et al. |
| 2011/0280916 A1 | 11/2011 | Blondino et al. |
| 2013/0109747 A1 | 5/2013 | Whittle |

FOREIGN PATENT DOCUMENTS

| | | |
|---|---|---|
| GB | 2461681 A | 1/2010 |
| WO | 2007087431 A2 | 8/2007 |
| WO | 2009120889 | 10/2009 |

OTHER PUBLICATIONS

International Search Report and the Written Opinion for corresponding application PCT/US14/52699 dated Nov. 26, 2014.
Panchagnula R. et al., Transdermal delivery of naloxone: effect of water, propylene glycol, ethanol and their binary combinations on permeation through rat skin, Int J Pharm, May 21, 2001 219(1-2), 95-105.
Prausnitz M.R., et al., Transdermal drug delivery, Nat Biotechnol, Nov. 2008, 26(11), 1261-1268.

*Primary Examiner* — Ernst V Arnold
(74) *Attorney, Agent, or Firm* — Wood, Phillips, Katz, Clark & Mortimer

(57) ABSTRACT

The invention provides liquid formulations containing buprenorphine, a pharmaceutically acceptable salt thereof, or a derivative thereof. The invention further provides liquid formulations containing buprenorphine and naloxone, pharmaceutically acceptable salts thereof or derivatives thereof. The invention further provides a method of treating pain or opioid dependence by administering liquid formulations containing buprenorphine or a combination of buprenorphine and naloxone, a pharmaceutically acceptable salt thereof, or a derivative thereof to a patient in need thereof.

20 Claims, 3 Drawing Sheets
(3 of 3 Drawing Sheet(s) Filed in Color)

LIQUID BUPRENORPHINE FORMULATIONS

FIELD OF THE INVENTION

The invention is directed to liquid formulations containing buprenorphine, a pharmaceutically acceptable salt thereof, or a derivative thereof. The invention is further directed to liquid formulations containing buprenorphine and naloxone, pharmaceutically acceptable salts thereof or derivatives thereof. The invention is further directed to a method of treating pain or opioid dependence by administering liquid formulations containing buprenorphine or buprenorphine and naloxone, pharmaceutically acceptable salts thereof, or derivatives thereof to a patient in need thereof.

BACKGROUND OF THE INVENTION

Buprenorphine is a semi-synthetic opioid and a partial μ-opioid receptor agonist and has the following structure:

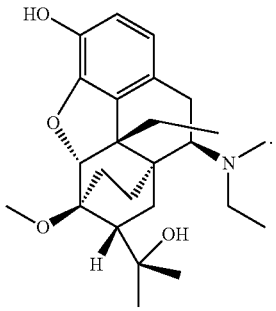

Activation of the μ-opioid receptor leads to antinociception and is the pathway by which opioids such as morphine and fentanyl reduce acute and chronic pain. Buprenorphine has advantages over other opioids such as morphine and fentanyl in that it is only a partial instead of a full agonist of the opioid receptor-like receptor 1 ("ORL1"). Activation of ORL1 has been reported to weaken the analgesic effect induced by the activation of the μ-opioid receptor. Additionally, buprenorphine is an antagonist of δ- and κ-opioid receptors, whose activation has anti-analgesic and psychotomimetic effects, respectively. Buprenorphine is also useful in the management of opioid dependence. The slow binding of buprenorphine to the μ-opioid receptor along with its strong affinity allows for pain management at relatively low blood concentrations and the slow disassociation of buprenorphine from the μ-opioid receptor results in a lack of withdrawal symptoms.

Buprenorphine is currently available in transdermal patches, intravenous injection, tablet and film strip formulations. Commercially available buprenorphine formulations include Butrans® (Butrans is a registered trademark of Purdue Pharma L.P.), a 7 day transdermal patch that releases buprenorphine at 5, 10 or 20 mcg/hr, and Temgesic, a 0.2 mg sublingual tablet, are used for the treatment of chronic pain. Buprenexm (Buprenex is a registered trademark of Reckitt Benckiser Healthcare (UK) Limited) is a 0.3 mg/mL injectable solution used for the treatment of acute pain. Subutex® (Subutex is a registered trademark of Reckitt Benckiser Healthcare (UK) Limited) and Suboxone® (Suboxone is a registered trademark of Reckitt Benckiser Healthcare (UK) Limited) are tablets used in the treatment of opioid dependence. Subutex® is available in 2 mg and 8 mg sublingual doses of buprenorphine. Suboxone® contains both buprenorphine and naloxone in a 4:1 ratio. Suboxone® is available in tablet form in 2 mg and 8 mg doses. Suboxone® is also available in a sublingual film strip formulation that dissolves faster and is not lost by accidental swallowing.

Naloxone has the following structure and is synthesized from thebaine:

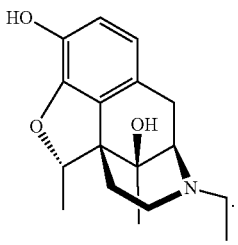

Naloxone is most commonly used to treat patients suffering from opioid dependence or overdose because it is a competitive μ-opioid antagonist that blocks the effects of opioids.

While there are various formulations currently available, there exists a need in the art for a liquid (i.e., sublingual or intranasal) spray formulation containing buprenorphine or buprenorphine and naloxone, pharmaceutically acceptable salts thereof, or derivatives thereof. Such a formulation should be safe, be easy to administer, have a high bioavailability, and be storage stable.

SUMMARY OF THE INVENTION

In one embodiment, the present invention is directed to a liquid formulation comprising an effective amount of buprenorphine, a pharmaceutically acceptable salt thereof, or a derivative thereof, water as a solvent, and a mixture of an alcohol and a glycol as a cosolvent.

In one embodiment, the present invention is directed to a liquid formulation comprising:
  an effective amount of buprenorphine, a pharmaceutically acceptable salt thereof, or a derivative thereof;
  naloxone, a pharmaceutically acceptable salt thereof, or a derivative thereof;
  water as a solvent; and
  a mixture of an alcohol and a glycol as a cosolvent.

In one embodiment, the present invention is directed to a liquid formulation comprising an effective amount of buprenorphine, a pharmaceutically acceptable salt thereof, or a derivative thereof wherein the formulation has a pH from about 3.5 to about 5.5.

In one embodiment, the present invention is directed to a liquid formulation comprising:
  an effective amount of buprenorphine, a pharmaceutically acceptable salt thereof, or a derivative thereof;
  water as a solvent;
  a mixture of an alcohol and a glycol as a cosolvent; and
  an antioxidant.

In one embodiment, the present invention is directed to a liquid formulation comprising:
  an effective amount of buprenorphine, a pharmaceutically acceptable salt thereof, or a derivative thereof;
  water as a solvent;
  a cosolvent selected from the group consisting of an alcohol and a glycol or a mixture thereof; and
  an antioxidant.

In one embodiment, the present invention is directed to a liquid formulation comprising:
an effective amount of buprenorphine, a pharmaceutically acceptable salt thereof, or a derivative thereof;
water as a solvent;
a cosolvent selected from the group consisting of an alcohol and a glycol or a mixture thereof; and
an antioxidant.

In one embodiment, the present invention is directed to a liquid formulation comprising:
an effective amount of buprenorphine, a pharmaceutically acceptable salt thereof, or a derivative thereof;
water as a solvent;
a mixture of an alcohol and a glycol as a cosolvent; and
an antioxidant selected from the group consisting of butylated hydroxyanisole ("BHA"), butylated hydroxytoluene ("BHT"), methionine, sodium ascorbate, sodium thiosulfate, thioglycerol, cysteine hydrochloride monohydrate and a mixture thereof.

In one embodiment, the present invention is directed to a liquid formulation comprising:
an effective amount of buprenorphine, a pharmaceutically acceptable salt thereof, or a derivative thereof;
water as a solvent;
a mixture of ethanol and propylene glycol as a cosolvent; and
an antioxidant selected from the group consisting of BHA, BHT, methionine, sodium ascorbate, sodium thiosulfate and thioglycerol, cysteine hydrochloride monohydrate or a mixture thereof.

In one embodiment, the present invention is directed to a liquid formulation comprising:
an effective amount of buprenorphine, a pharmaceutically acceptable salt thereof, or a derivative thereof;
water as a cosolvent;
a cosolvent selected from the group consisting of ethanol, propylene glycol, and a mixture thereof;
an antioxidant selected from the group consisting of BHA, BHT, methionine, sodium ascorbate, sodium thiosulfate, thioglycerol, cysteine hydrochloride monohydrate and a mixture thereof; and
a permeation enhancer.

In one embodiment, the present invention is directed to a liquid formulation comprising:
an effective amount of buprenorphine, a pharmaceutically acceptable salt thereof, or a derivative thereof;
water as a solvent;
a cosolvent selected from the group consisting of ethanol, propylene glycol, and a mixture thereof;
an antioxidant selected from the group consisting of BHA, BHT, methionine, sodium ascorbate, sodium thiosulfate, thioglycerol, cysteine hydrochloride monohydrate and a mixture thereof; and
menthol as a permeation enhancer.

In one embodiment, the present invention is directed to a liquid formulation comprising:
an effective amount of buprenorphine, a pharmaceutically acceptable salt thereof, or a derivative thereof;
water as a solvent;
a cosolvent selected from the group consisting of ethanol, propylene glycol, and a mixture thereof;
an antioxidant selected from the group consisting of BHA, BHT, methionine, sodium ascorbate, sodium thiosulfate, thioglycerol, cysteine hydrochloride monohydrate and a mixture thereof; and
a pH adjustor.

In one embodiment, the present invention is directed to a liquid formulation comprising:
an effective amount of buprenorphine, a pharmaceutically acceptable salt thereof, or a derivative thereof;
water as a solvent;
a cosolvent selected from the group consisting of ethanol, propylene glycol, and a mixture thereof;
an antioxidant selected from the group consisting of BHA, BHT, methionine, sodium ascorbate, sodium thiosulfate, thioglycerol, cysteine hydrochloride monohydrate and a mixture thereof; and
citric acid as a pH adjustor selected from the group consisting of citric acid, sodium hydroxide and a mixture thereof.

In one embodiment, the present invention is directed to a liquid formulation comprising:
an effective amount of buprenorphine, a pharmaceutically acceptable salt thereof, or a derivative thereof;
water as a solvent;
a solubilizer selected from the group consisting of cyclodextrins such as hydropropyl beta-cyclodextrin ("HPβCD"), sulfobutylether cyclodextrin, and a mixture thereof; and
an antioxidant selected from the group consisting of BHA, BHT, methionine, sodium ascorbate, sodium thiosulfate, thioglycerol, cysteine hydrochloride monohydrate and a mixture thereof.

When the application describes the amounts of buprenorphine and naloxone, all the amounts refer to buprenorphine base and naloxone base, respectively, unless otherwise indicated.

In one embodiment, the present invention is directed to a sublingual spray formulation comprising:
an amount of buprenorphine from about 0.01% to about 10% w/w;
an amount of water from about 10% to about 95% w/w;
an amount of ethanol as a cosolvent from about 10% to about 80% w/w;
a glycol in an amount from about 0.5% to about 50% w/w; and
an amount of antioxidant from about 0.0001% to about 0.5% w/w; and
optionally, menthol in an amount of about 0.005% w/w to about 0.5% w/w as a permeation enhancer.

In one embodiment, the present invention is directed to a sublingual spray formulation comprising:
an amount of buprenorphine from about 0.06% to about 1.5% w/w;
an amount of water from about 38% to about 40% w/w;
a cosolvent consisting of a mixture of ethanol in an amount of 55% w/w and propylene glycol in an amount of about 5% w/w;
an antioxidant consisting of a mixture of butylated hydroxyanisole (BHA) in an amount of about 0.01% w/w and butylated hydroxytoluene (BHT) in an amount of about 0.005% w/w; and
menthol in an amount of about 0.05% w/w.

In one embodiment, the present invention is directed to a sublingual spray formulation comprising:
buprenorphine, a pharmaceutically acceptable salt thereof or a derivative thereof in an amount from about 0.05% to about 5% w/w;
water as a solvent in an amount from about 20% to about 60% w/w;
a cosolvent consisting of a mixture of an alcohol from about 30% w/w to about 60% w/w and a glycol in an amount from about 1% to about 10% w/w;

an antioxidant in an amount from about 0.001% to about 0.1% w/w; and
menthol from about 0.01% w/w to about 0.1% w/w;
wherein the % w/w is of the total formulation.

In one embodiment, the present invention is directed to a sublingual spray formulation comprising:
buprenorphine, a pharmaceutically acceptable salt thereof or a derivative thereof in an amount from about 0.06% to about 1.5% w/w;
water as a solvent in an amount of from about 38% to about 40% w/w;
a cosolvent consisting of a mixture of ethanol in an amount of 55% w/w and propylene glycol in an amount of about 5% w/w;
the antioxidant consisting of a mixture of butylated hydroxyanisole (BHA) in an amount of about 0.01% w/w and butylated hydroxytoluene (BHT) in an amount of about 0.005% w/w; and
menthol at an amount of about 0.05% w/w;
wherein the % w/w is of the total formulation.

In one embodiment, the present invention is directed to a sublingual spray formulation comprising:
buprenorphine, a pharmaceutically acceptable salt thereof or a derivative thereof at an amount from about 0.05% to about 15% w/w;
naloxone, a pharmaceutically acceptable salt thereof or a derivative thereof at an amount from about 0.005% to about 5% w/w;
water as a solvent in an amount from about 10% w/w to about 95% w/w;
a cosolvent consisting of a mixture of an alcohol in an amount from about 10% to about 80% w/w and a glycol in an amount from about 0.5% w/w to about 50% w/w;
an antioxidant in an amount from about 0.001% to about 0.2% w/w; and
a chelating agent in an amount from about 0.001% to about 0.1% w/w;
wherein the % w/w is of the total formulation.

In one embodiment, the present invention is directed to a sublingual spray formulation comprising:
buprenorphine, a pharmaceutically acceptable salt thereof or a derivative thereof at an amount from about 0.05% to about 10% w/w;
naloxone, a pharmaceutically acceptable salt thereof or a derivative thereof at an amount from about 0.1% to about 3% w/w;
water as a solvent in an amount from about 20% w/w to about 45% w/w;
a cosolvent consisting of a mixture of ethanol in an amount of 50% w/w to about 60% w/w and propylene glycol in an amount of about 4% w/w to 6% w/w;
an antioxidant selected from a group consisting of butylated hydroxyanisole, butylated hydroxytoluene, methionine, sodium ascorbate, sodium thiosulfate, thioglycerol, cysteine hydrochloride monohydrate, and a mixture thereof at an amount of about 0.01% to about 0.1 w/w;
disodium edetate as a chelating agent at an amount of about 0.001% to about 0.01% w/w; and
menthol at an amount of about 0.005% to 0.5% w/w;
wherein the % w/w is of the total formulation.

In one embodiment, the present invention is directed to a sublingual spray formulation comprising:
buprenorphine, a pharmaceutically acceptable salt thereof or a derivative thereof at an amount from about 0.6% to about 10%/o w/w;
naloxone, a pharmaceutically acceptable salt thereof or a derivative thereof at an amount from about 0.1% to about 3.0% w/w;
menthol at an amount of about 0.05% w/w;
disodium edetate at an amount of about 0.005% w/w;
sodium ascorbate in an amount of about 0.02%;
ethanol in an amount of about 55%;
propylene glycol in an amount from about 5% w/w;
water in an amount from about 25% w/w to 40% w/w;
wherein the % w/w is of the total formulation.

In one embodiment, the present invention is directed to a sublingual spray formulation comprising:
buprenorphine, a pharmaceutically acceptable salt thereof or a derivative thereof at an amount from about 0.05% to about 9.5% w/w;
naloxone, a pharmaceutically acceptable salt thereof or a derivative thereof at an amount from about 0.2% to about 2.7% w/w;
water as a solvent in an amount from about 27.4% w/w to 39.7% w/w;
a cosolvent consisting of a mixture of ethanol in an amount from about 55% w/w and propylene glycol in an amount from about 5% w/w; and
an antioxidant selected from a group consisting of butylated hydroxyanisole, butylated hydroxytoluene, methionine, sodium ascorbate, sodium thiosulfate, thioglycerol, cysteine hydrochloride monohydrate and a mixture thereof in an amount from about 0.001% to about 0.2% w/w.

In one embodiment, the present invention is directed to a sublingual spray formulation comprising:
buprenorphine, a pharmaceutically acceptable salt thereof or a derivative thereof at an amount from about 0.05% to about 9.5% w/w;
naloxone, a pharmaceutically acceptable salt thereof or a derivative thereof at an amount from about 0.005% to about 2.7% w/w;
water as a solvent in an amount from about 27.4% w/w to 39.7% w/w;
a cosolvent consisting of a mixture of ethanol in an amount of about 55% w/w and propylene glycol in an amount of about 5% w/w; and
an antioxidant selected from a group consisting of butylated hydroxyanisole, butylated hydroxytoluene, methionine, sodium ascorbate, sodium thiosulfate, thioglycerol, cysteine hydrochloride monohydrate, and a mixture thereof in an amount from about 0.001% to about 0.2% w/w.

In one embodiment, the present invention is directed to a sublingual spray formulation comprising:
buprenorphine, a pharmaceutically acceptable salt thereof or a derivative thereof at an amount from about 0.05% to about 9.5% w/w;
naloxone, a pharmaceutically acceptable salt thereof or a derivative thereof at an amount from about 0.005% to about 3% w/w;
water as a solvent in an amount from about 27.4% w/w to 39.7% w/w;
a cosolvent consisting of a mixture of ethanol in an amount of about 55% w/w and propylene glycol in an amount of about 5% w/w;
an antioxidant selected from a group consisting of butylated hydroxyanisole, butylated hydroxytoluene, methionine, sodium ascorbate, sodium thiosulfate, thioglycerol, cysteine hydrochloride monohydrate, and a mixture thereof; and ethylenediaminetetraacetic acid disodium (disodium edetate) as a chelating agent in an amount of about 0.005% w/w or citric acid as a pH adjustor in an amount from about 0.0025 to 10% w/w.

In certain embodiments, the liquid formulations are the liquid spray formulations.

In certain embodiments, the liquid formulations of the present invention contain naloxone in an amount that discourages improper administration of the formulations. When the naloxone containing formulations are properly administered, the naloxone is delivered at a rate that is below that which would be therapeutic. In this context, "therapeutic" refers to an amount of naloxone that would block the effects of the buprenorphine that is concurrently administered in the sublingual spray formulation. If the formulations are improperly used, however, the naloxone in the formulation could be sufficient to block the effects of buprenorphine.

In certain embodiments, the present invention is directed to methods for treating pain comprising administering a liquid formulation of the present invention to a patient.

In certain embodiments, the present invention is directed to methods for treating opioid dependence comprising administering a liquid formulation of the present invention to a patient.

In an embodiment, the present invention is directed to sublingual spray formulations wherein the $C_{max}$ (ng/mL) of buprenorphine is from about 0.6 to about 1.5. In one preferred embodiment, the $C_{max}$ (ng/mL) of buprenorphine is 0.76 following sublingual administration. In another preferred embodiment, the $C_{max}$ (ng/mL) of buprenorphine is 1.38 following sublingual administration.

In yet another embodiment, the present invention is directed to sublingual spray formulations wherein the $T_{max}$ of buprenorphine is from about 1.5 to about 1.9 hours. In a preferred embodiment, the $T_{max}$ of buprenorphine is about 1.75 hours following sublingual administration.

In yet another embodiment, the present invention is directed to sublingual spray formulations wherein the $C_{max}$ (ng/mL) of buprenorphine is from about 1.2 to about 1.5. In a preferred embodiment, the $C_{max}$ (ng/mL) of buprenorphine is about 1.38 following sublingual administration.

In a further embodiment, the present invention is directed to sublingual spray formulations wherein the $T_{max}$ of buprenorphine is from about 1.2 to about 1.7 hours. In a preferred embodiment, the $T_{max}$ of buprenorphine is about 1.5 hours following sublingual administration.

In a further embodiment, the present invention is directed to sublingual spray formulations wherein the $AUC_{0-T}$ (ng·h/mL) of buprenorphine is from about 2 to about 6 for 0.5 mg dose, and from about 7 to about 11 for 1 mg dose.

In a further embodiment, the present invention is directed to sublingual spray formulations wherein the $AUC_{0-\infty}$ (ng·h/mL) of buprenorphine is from about 2 to about 6 for 0.5 mg dose, and from about 7 to about 11 for 1 mg dose.

In another embodiment, the present invention is directed to sublingual spray formulations wherein greater than 98% of the formulation particles are greater than 10 microns in diameter during administration.

In another embodiment, the present invention is directed to sublingual spray formulations wherein the mean Dv(10) is from about 10 to about 40 microns during administration.

In another embodiment, the present invention is directed to sublingual spray formulations wherein the mean Dv(50) is from about 30 to about 80 microns during administration.

In another embodiment, the present invention is directed to sublingual spray formulations wherein the mean Dv(90) is from about 80 to about 200 microns during administration.

In a further embodiment, the present invention is directed to sublingual spray formulations that when administered provide a spray plume ovality ratio of from about 1.1 to 2.4.

In yet another embodiment, the invention is directed to sublingual formulations that when administered provide a plume width of from about 25 to about 45 millimeters.

In a further embodiment, the invention is directed to sublingual formulations that when administered provide a plume angle of from about 30 to about 55 degrees.

In yet another embodiment, the invention is directed to sublingual formulations that when administered provide a D(4,3) of 55 to 95 microns.

In an additional embodiment, the invention is directed to sublingual formulations that when administered provide a spray span ((Dv90−Dv10)/Dv50) of from about 1.2 to about 3.3.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
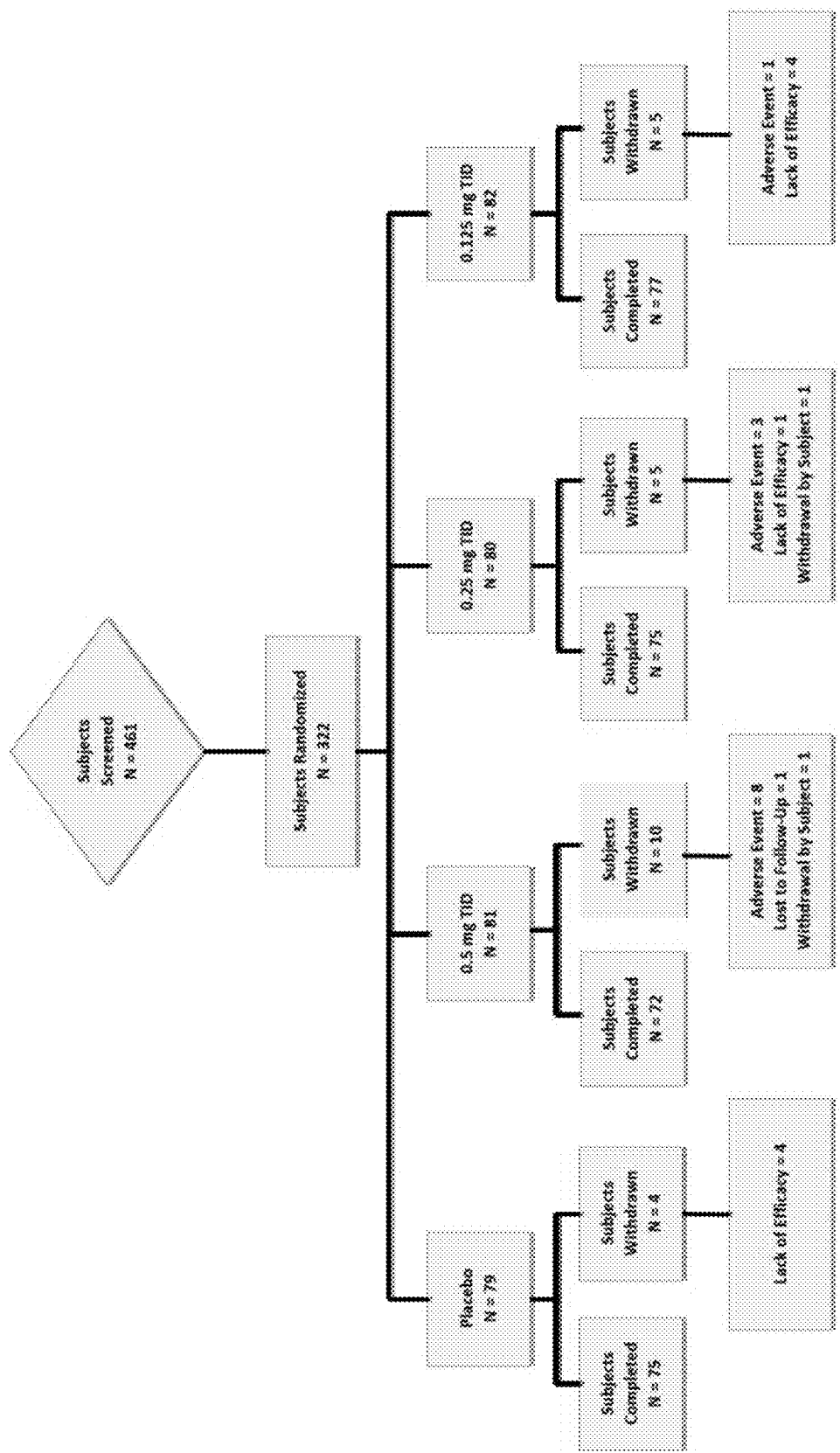
FIG. 1 depicts a flow chart describing the disposition of the study of the effect of buprenorphine sublingual spray to treat bunionectomy-related pain.

The present invention is directed to a liquid formulation comprising an effective amount of buprenorphine or buprenorphine and naloxone, pharmaceutically acceptable salts thereof, or derivatives thereof. The present invention further relates to a method of treating pain or opioid dependence by administering an effective amount of a liquid formulation of the present invention to a patient in need thereof.

The present invention is further directed to a liquid formulation comprising an effective amount of buprenorphine or buprenorphine and naloxone, pharmaceutically acceptable salts thereof, or derivatives thereof, a solvent, a cosolvent and an antioxidant.

Applicants developed new liquid buprenorphine and buprenorphine/naloxone formulations that unexpectedly are storage stable, safe and effective. Specifically, Applicants were surprised that the formulations were stable at high temperatures (40 degrees Celsius) for an extended period of time (see Examples 1 and 2 below). Further, Applicants unexpectedly found that the formulations provided a quick onset of action and bioavailability (as demonstrated by pharmacokinetic studies, see Example 3 below). The formulations upon administration exhibit excellent droplet size distribution, as well.

As used herein the term "patient" refers but is not limited to a person that is being treated for pain, opioid dependence or another affliction or disease that can be treated with buprenorphine.

As used herein the term "pharmaceutically acceptable" refers to ingredients that are not biologically or otherwise undesirable in a sublingual dosage form.

As used herein the term "effective amount" refers to the amount necessary to treat a patient in need thereof.

As used herein the term "liquid" refers to a sublingual, intranasal or otherwise administered through a mouth or a nose formulation.

As used herein the term "sublingual" refers to administration of a substance via the mouth in such a way that the substance is rapidly absorbed via the blood vessels under the tongue.

As used herein the term "intranasal" refers to administration of the composition to any portion of the nasal epithelium.

Pharmaceutically acceptable salts that can be used in accordance with the current invention include but are not limited to hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts.

In preferred embodiments the pharmaceutically acceptable salt is hydrochloride.

Derivatives of buprenorphine that can be used in accordance with the current invention include but are not limited norbuprenorphine, thenorphine, demethoxybuprenorphine and esters and diastereomers of buprenorphine.

The solvent used with the present invention is United States Pharmacopeia ("USP") purified water.

Cosolvents that can be used in accordance with the current invention are alcohols, and glycols or a mixture thereof.

Alcohols that can be used in accordance with the current invention include but are not limited to methanol, ethanol, propyl alcohol, and butyl alcohol.

Glycols that can be used in accordance with the current invention include but are not limited to propylene glycol, butylene glycol and polyethylene glycols such as PEG 200 and PEG 400 and the like.

In preferred embodiments the cosolvent is ethanol or propylene glycol or a mixture thereof.

In more preferred embodiments the amount of cosolvent included in the formulation is from about 5% to about 90% w/w.

In other more preferred embodiments the amount of cosolvent included in the formulation is from about 2 to about 10% propylene glycol. In a most preferred embodiment the amount of cosolvent is about 5% w/w propylene glycol.

In other more preferred embodiments the amount of cosolvent included in the formulation is about 40% w/w to about 60% w/w ethanol. In a most preferred embodiment the amount of cosolvent is about 55% w/w ethanol.

In other more preferred embodiments the cosolvent is a mixture of propylene glycol at about 5% w/w and ethanol at about 55% w/w.

Solubilizers that can be used in accordance with the current invention are hydroxypropyl beta-cyclodextrin ("HPPCD") and sulfobutylether cyclodextrin or a mixture thereof.

In preferred embodiments the solubilizer is HPβCD.

In more preferred embodiments the amount of HPβCD is from about 10% w/w to 40% w/w. In a most preferred embodiment the amount of HPβCD is about 30% w/w.

Antioxidants that can be used in accordance with the current invention include but are not limited to butylated hydroxyanisole ("BHA"), butylated hydroxytoluene ("BHT"), methionine, sodium ascorbate, sodium thiosulfate and thioglycerol, cysteine hydrochloride monohydrate or a mixture thereof.

In preferred embodiments the amount of antioxidant included in the formulation is from about 0.001% to about 0.05% w/w.

In more preferred embodiments the amount of antioxidant is about 0.01% w/w of BHA.

In other more preferred embodiments the antioxidant is a mixture of about 0.01% w/w of BHA and about 0.005% w/w of BHT.

In other more preferred embodiments the antioxidant is about 0.01% w/w of sodium thiosulfate.

In other more preferred embodiments the antioxidant is about 0.02% w/w of sodium ascorbate.

Permeation enhancers that can be used in accordance with the current invention include but are not limited to menthol, Tween® 80 (Tween is a registered trademark of Uniqema Americas, LLC), sodium lauryl sulfate, glyceryl oleate, oleic acid, cetylpyridium chloride, and sodium desoxy cholate.

In preferred embodiments the amount of permeation enhancer is from about 0.001% to about 0.1% w/w.

In more preferred embodiments the amount of permeation enhancer is about 0.05% w/w of menthol.

Chelating agents that can be used in accordance with the present invention include but are not limited to ethylenediaminetetraacetic acid disodium ("disodium edetate" or edetate disodium dihydrate").

In preferred embodiments the amount of disodium edetate is about 0.005% to about 0.01% w/w.

Formulations of the present invention may have a pH range from about 3.0 to about 7.0, preferably from about 3.5 to about 5.5 and more preferably from about 3.8 to about 5.1. pH adjustors that can be used in accordance with the present invention include but are not limited to citric acid, sodium hydroxide and a mixture thereof. In preferred embodiments the amount of citric acid is from about 2% to about 20% w/w. In more preferred embodiments the amount of citric acid is about 15%. In other more preferred embodiments the amount of citric acid is about 10%.

As used herein, all numerical values relating to amounts, weights, and the like, that are defined as "about" each particular value is plus or minus 10%°. For example, the phrase "about 10% w/w" is to be understood as "9% to 11% w/w." Therefore, amounts within 10% of the claimed value are encompassed by the scope of the claims.

As used herein "% w/w" refers to the percent weight of the total formulation.

Representative Embodiments

In one embodiment, the present invention is directed to a sublingual spray formulation comprising:
  an amount of buprenorphine from about 0.01% to about 10% w/w;
  an amount of water from about 10% to about 95% w/w;
  an amount of cosolvent from about 10% to about 80% w/w;
  a glycol in an amount from about 0.5% to about 50% w/w; and
  an amount of antioxidant from about 0.0001% to about 0.5% w/w; and
  optionally, menthol in an amount of about 0.005% w/w to about 0.5% w/w as a permeation enhancer.

In one embodiment, the present invention is directed to a sublingual spray formulation comprising:

an amount of buprenorphine from about 0.06% to about 1.5% w/w;
an amount of water from about 38% to about 40% w/w;
a cosolvent consisting of a mixture of ethanol in an amount of 55% w/w
and propylene glycol in an amount of about 5% w/w;
an antioxidant consisting of a mixture of butylated hydroxyanisole (BHA) in an amount of about 0.01% w/w and butylated hydroxytoluene (BHT) in an amount of about 0.005% w/w; and
menthol in an amount of about 0.05% w/w.

In one embodiment, the present invention is directed to a sublingual spray formulation comprising:
buprenorphine, a pharmaceutically acceptable salt thereof or a derivative thereof in an amount from about 0.05% to about 5% w/w;
water as a solvent in an amount from about 20% to about 60% w/w;
a cosolvent consisting of a mixture of an alcohol from about 30% w/w to about 60% w/w and a glycol in an amount from about 1% to about 10% w/w;
an antioxidant in an amount from about 0.001% to about 0.1% w/w; and
menthol from about 0.01% w/w to about 0.1% w/w;
wherein the % w/w is of the total formulation.

In one embodiment, the present invention is directed to a sublingual spray formulation comprising:
buprenorphine, a pharmaceutically acceptable salt thereof or a derivative thereof in an amount from about 0.06% to about 1.5% w/w;
water as a solvent in an amount of from about 38% to about 40% w/w;
a cosolvent consisting of a mixture of ethanol in an amount of 55% w/w and propylene glycol in an amount of about 5% w/w;
the antioxidant consisting of a mixture of butylated hydroxyanisole (BHA) in an amount of about 0.01% w/w and butylated hydroxytoluene (BHT) in an amount of about 0.005% w/w; and
menthol at an amount of about 0.05% w/w;
wherein the % w/w is of the total formulation.

In one embodiment, the present invention is directed to a sublingual spray formulation comprising:
buprenorphine, a pharmaceutically acceptable salt thereof or a derivative thereof at an amount from about 0.05% to about 15% w/w;
naloxone, a pharmaceutically acceptable salt thereof or a derivative thereof at an amount from about 0.005% to about 5% w/w;
water as a solvent in an amount from about 10% w/w to about 95% w/w;
a cosolvent consisting of a mixture of an alcohol in an amount from about 10% to about 80% w/w and a glycol in an amount from about 0.5% w/w to about 50% w/w;
an antioxidant in an amount from about 0.001% to about 0.2% w/w; and
a chelating agent in an amount from about 0.001% to about 0.1% w/w;
wherein the % w/w is of the total formulation.

In one embodiment, the present invention is directed to a sublingual spray formulation comprising:
buprenorphine, a pharmaceutically acceptable salt thereof or a derivative thereof at an amount from about 0.05% to about 10% w/w;
naloxone, a pharmaceutically acceptable salt thereof or a derivative thereof at an amount from about 0.1% to about 3% w/w;
water as a solvent in an amount from about 20% w/w to about 45% w/w;
a cosolvent consisting of a mixture of ethanol in an amount of 50% w/w to about 60% w/w and propylene glycol in an amount of about 4% w/w to 6% w/w;
an antioxidant selected from a group consisting of butylated hydroxyanisole, butylated hydroxytoluene, methionine, sodium ascorbate, sodium thiosulfate, thioglycerol, cysteine hydrochloride monohydrate, and a mixture thereof at an amount of about 0.01% to about 0.1 w/w;
disodium edetate as a chelating agent at an amount of about 0.001% to about 0.01% w/w; and
menthol at an amount of about 0.005% to 0.5% w/w;
wherein the % w/w is of the total formulation.

In one embodiment, the present invention is directed to a sublingual spray formulation comprising:
buprenorphine, a pharmaceutically acceptable salt thereof or a derivative thereof at an amount from about 0.6% to about 10% w/w;
naloxone, a pharmaceutically acceptable salt thereof or a derivative thereof at an amount from about 0.1% to about 3.0% w/w;
menthol at an amount of about 0.05% w/w;
disodium edetate at an amount of about 0.005% w/w;
sodium ascorbate in an amount of about 0.02%;
ethanol in an amount of about 55%;
propylene glycol in an amount from about 5% w/w;
water in an amount from about 25% w/w to 40% w/w;
wherein the % w/w is of the total formulation.

In one embodiment, the present invention is directed to a sublingual spray formulation comprising:
buprenorphine, a pharmaceutically acceptable salt thereof or a derivative thereof at an amount from about 0.05% to about 9.5% w/w;
naloxone, a pharmaceutically acceptable salt thereof or a derivative thereof at an amount from about 0.2% to about 2.7% w/w;
water as a solvent in an amount from about 27.4% w/w to 39.7% w/w;
a cosolvent consisting of a mixture of ethanol in an amount from about 55% w/w and propylene glycol in an amount from about 5% w/w; and
an antioxidant selected from a group consisting of butylated hydroxyanisole, butylated hydroxytoluene, methionine, sodium ascorbate, sodium thiosulfate, thioglycerol, cysteine hydrochloride monohydrate and a mixture thereof in an amount from about 0.001% to about 0.2% w/w.

In one embodiment, the present invention is directed to a sublingual spray formulation comprising:
buprenorphine, a pharmaceutically acceptable salt thereof or a derivative thereof at an amount from about 0.05% to about 9.5% w/w;
naloxone, a pharmaceutically acceptable salt thereof or a derivative thereof at an amount from about 0.005% to about 2.7% w/w;
water as a solvent in an amount from about 27.4% w/w to 39.7% w/w;
a cosolvent consisting of a mixture of ethanol in an amount of about 55% w/w and propylene glycol in an amount of about 5% w/w; and
an antioxidant selected from a group consisting of butylated hydroxyanisole, butylated hydroxytoluene, methionine, sodium ascorbate, sodium thiosulfate, thioglycerol, cysteine hydrochloride monohydrate, and a mixture thereof in an amount from about 0.001% to about 0.2% w/w.

In one embodiment, the present invention is directed to a sublingual spray formulation comprising:
  buprenorphine, a pharmaceutically acceptable salt thereof or a derivative thereof at an amount from about 0.05% to about 9.5% w/w;
  naloxone, a pharmaceutically acceptable salt thereof or a derivative thereof at an amount from about 0.005% to about 3% w/w;
  water as a solvent in an amount from about 27.4% w/w to 39.7% w/w;
  a cosolvent consisting of a mixture of ethanol in an amount of about 55% w/w and propylene glycol in an amount of about 5% w/w;
  an antioxidant selected from a group consisting of butylated hydroxyanisole, butylated hydroxytoluene, methionine, sodium ascorbate, sodium thiosulfate, thioglycerol, cysteine hydrochloride monohydrate, and a mixture thereof; and
  ethylenediaminetetraacetic acid disodium (disodium edetate) as a chelating agent in an amount of about 0.005% w/w or citric acid as a pH adjustor in an amount from about 0.0025 to 10% w/w.

In one embodiment, the sublingual spray formulation comprises:
  an amount of buprenorphine of about 0.54% w/w;
  an amount of water of about 39.4% w/w;
  a cosolvent as a mixture of ethanol in an amount of about 55% w/w and propylene glycol in an amount of about 5% w/w;
  an antioxidant as a mixture of BHA in an amount of about 0.01% w/w and BHT in an amount of about 0.005% w/w; and
  menthol as a permeation enhancer in an amount of about 0.05% w/w.

In one embodiment, the sublingual spray formulation comprises:
  an amount of buprenorphine of about 0.54% w/w;
  an amount of water of about 39.4% w/w;
  a cosolvent as a mixture of ethanol in an amount of about 55% w/w and propylene glycol in an amount of about 5% w/w;
  sodium thiosulfate as an antioxidant in an amount of about 0.01% w/w;
  menthol as a permeation enhancer in an amount of about 0.05% w/w; and
  citric acid as a pH adjustor in an amount of about 0.002% w/w.

In one embodiment, the sublingual spray formulation comprises:
  an amount of buprenorphine of about 0.54% w/w;
  an amount of water of about 39.39% w/w;
  a cosolvent as a mixture of ethanol in an amount of about 55% w/w and propylene glycol in an amount of about 5% w/w;
  sodium ascorbate as an antioxidant in an amount of about 0.01% w/w;
  menthol as a permeation enhancer in an amount of about 0.05% w/w; and
  disodium edetate as a chelating agent in an amount of about 0.01% w/w.

In one embodiment, the sublingual spray formulation comprises:
  an amount of buprenorphine of about 0.54% w/w;
  an amount of water of about 39.45% w/w;
  a cosolvent as a mixture of ethanol in an amount of about 55% w/w and propylene glycol in an amount of about 5% w/w; and
  BHA as an antioxidant in an amount of about 0.01% w/w.

In one embodiment, the sublingual spray formulation comprises:
  an amount of buprenorphine of about 8.602% w/w;
  an amount of naloxone of about 2.44% w/w;
  an amount of water of about 29% w/w;
  an amount of sodium thiosulfate of about 0.01% w/w; and
  an amount of citric acid of about 0.0025% w/w.

In one embodiment, the sublingual spray formulation comprises:
  an amount of buprenorphine of about 8.602% w/w;
  an amount of naloxone of about 2.44% w/w;
  an amount of water of about 29% w/w;
  an amount of sodium thiosulfate of about 0.01% w/w; and
  an amount of disodium edetate of about 0.005% w/w.

In one embodiment, the sublingual spray formulation comprises:
  an amount of buprenorphine of about 8.602% w/w;
  an amount of naloxone of about 2.44% w/w;
  an amount of water of about 29% w/w;
  an antioxidant as a mixture of BHA in an amount of about 0.01% w/w and BHT in an amount of about 0.005% w/w; and
  an amount of disodium edetate of about 0.005% w/w.

In one embodiment, the sublingual spray formulation comprises:
  an amount of buprenorphine of about 8.602% w/w;
  an amount of naloxone of about 2.44% w/w;
  an amount of water of about 29% w/w;
  an amount of sodium ascorbate of about 0.02% w/w; and
  an amount of disodium edetate of about 0.005% w/w.

In one embodiment, the sublingual spray formulation comprises:
  an amount of buprenorphine of about 8.39% a w/w;
  an amount of naloxone of about 2.37% w/w;
  an amount of water of about 29% w/w;
  an amount of ethanol of about 55% w/w;
  an amount of propylene glycol of about 5% w/w;
  an amount of sodium ascorbate of about 0.02% w/w;
  an amount of disodium edetate of about 0.005% w/w; and
  an amount of menthol of about 0.05% w/w.

In one embodiment, the sublingual spray formulation comprises:
  an amount of buprenorphine of about 5.554% w/w;
  an amount of naloxone of about 1.57% w/w;
  an amount of water of about 33% w/w;
  an amount of ethanol of about 55% w/w;
  an amount of propylene glycol of about 5% w/w;
  an amount of sodium ascorbate of about 0.02% w/w;
  an amount of disodium edetate of about 0.005% w/w; and
  an amount of menthol of about 0.05% w/w.

In one embodiment, the sublingual spray formulation comprises:
  an amount of buprenorphine of about 2.84% w/w;
  an amount of naloxone of about 0.804% w/w;
  an amount of water of about 36% w/w;
  an amount of ethanol of about 55% w/w;
  an amount of propylene glycol of about 5% w/w;
  an amount of sodium ascorbate of about 0.02% w/w;
  an amount of disodium edetate of about 0.005% w/w; and
  an amount of menthol of about 0.05% w/w.

In one embodiment, the sublingual spray formulation comprises:
  an amount of buprenorphine of about 1.42% w/w;

an amount of naloxone of about 0.402% w/w;
an amount of water of about 38% w/w;
an amount of ethanol of about 55% w/w;
an amount of propylene glycol of about 5% w/w;
an amount of sodium ascorbate of about 0.02% w/w;
an amount of disodium edetate of about 0.005% w/w; and
an amount of menthol of about 0.05% w/w.

In one embodiment, the sublingual spray formulation comprises:
an amount of buprenorphine from about 0.813% to about 1.3% w/w, preferably 0.0813% w/w, 0.1625% w/w, 0.325% w/w, 0.65% w/w or 1.3% w/w;
an amount of BHA of about 0.01% w/w;
an amount of BHT of about 0.005% w/w;
an amount of ethanol of about 55% w/w;
an amount of propylene glycol of about 5% w/w; and
an amount of water from about 39.8537% to about 38.635% w/w, preferably 39.8537% w/w, 39.7725% w/w, 39.61% w/w, 39.285% w/w or 38.635% w/w.

The following examples are intended to illustrate the present invention and to teach one of ordinary skill in the art how to make and use the invention. They are not intended to be limiting in any way.

EXAMPLES

Example 1: Stable Buprenorphine Formulations

Method of Making the Formulations

Sublingual spray formulations were created by first degassing ethanol and USP purified water, separately. Next, the ethanol and purified water were each purged with nitrogen. Soluble excipients were then dissolved in either the ethanol or the purified water based on their solubility. Next, the solutions were combined. Active pharmaceutical ingredient/s was/were added to the final solution and mixed until dissolved.

Formulations

TABLE 1

Stable Sublingual Buprenorphine Spray Formulations

| Formulation | Control | #1 | #2 | #3 | #4 | #5 | #6 | #7 | #8 | #9 |
|---|---|---|---|---|---|---|---|---|---|---|
| Buprenorphine HCl | 0.538 | 0.538 | 0.538 | 0.538 | 0.538 | 0.538 | 0.538 | 0.538 | 0.538 | 0.538 |
| Water (USP) | 39.462 | 39.452 | 39.397 | 39.372 | 89.427 | 94.427 | 39.39 | 39.4 | 39.405 | 69.472 |
| Ethanol | 55 | 55 | 55 | 55 | 10 | | 55 | 55 | 55 | |
| Propylene Glycol | 5 | 5 | 5 | 5 | | 5 | 5 | 5 | 5 | |
| HPβCD | | | | | | | | | | 30 |
| BHA | | 0.01 | 0.01 | | | | | | | |
| BHT | | | 0.005 | | | | | | | |
| Sodium Ascorbate | | | | 0.02 | 0.02 | 0.02 | 0.01 | | | 0.02 |
| Sodium Thiosulfate | | | | | | | | 0.01 | | |
| Methionine | | | | | | | | | 0.005 | |
| Menthol | | | 0.05 | 0.05 | | | | 0.05 | 0.05 | 0.05 |
| Citric Acid | | | | 0.02 | 0.015 | 0.015 | | 0.002 | 0.002 | |
| Disodium Edetate | | | | | | | 0.01 | | | |
| pH | 5.09 | 4.99 | 5.11 | 4.71 | 4.01 | 4 | 4.43 | 3.9 | 3.85 | No Data | values = % w/w

Stability Data

The formulations listed in Table 1 were subject to stability test at 40° C.±2° C. under 75%±5% relative humidity for six months. Stability data was collected at zero, and six months. Assay and impurities were detected using high performance liquid chromatography with an ultraviolet detector. The assay was performed at 288 nm and indicated as a % of initial concentration. For all impurities, analysis was performed at 240 nm and expressed as a % area. Amounts of particular impurities are listed in Table 2 as a percentage of the area of each formulation along with amount of total impurities.

TABLE 2

Stability Data for Sublingual Buprenorphine Spray Formulations stored at 40° C. ± 2° C. under 75% ± 5% relative humidity.

| Time | Control | | #1 | | #2 | | #3 | | #4 | | #5 | |
|---|---|---|---|---|---|---|---|---|---|---|---|---|
| (m) | 0 | 6 | 0 | 6 | 0 | 6 | 0 | 6 | 0 | 6 | 0 | 6 |
| Assay | 100 | 104 | 100 | 104.2 | 100 | 104.1 | 100 | 103.3 | 100 | 102.7 | 100 | 99.2 |
| A | BQL | ND | BQL | ND | ND | ND | BQL | ND | ND | ND | ND | ND |
| B | ND | 0.27 | ND | 0.09 | ND | 0.06 | ND | 0.21 | ND | 0.05 | ND | 0.09 |
| D | ND | BQL | ND | ND | ND | ND | ND | ND | ND | ND | ND | ND |
| G | BQL | 0.64 | ND | 0.06 | ND | BQL | ND | 0.11 | 0.11 | 0.68 | 0.09 | 0.77 |
| H | ND | ND | ND | ND | ND | ND | ND | ND | ND | ND | ND | ND |
| Bisalkyl-buprenorphine | ND | ND | ND | 0.31 | ND | BQL | ND | ND | ND | ND | ND | ND |

TABLE 2-continued

Stability Data for Sublingual Buprenorphine Spray Formulations stored at 40° C. ± 2° C. under 75% ± 5% relative humidity.

| Unspecified | BQL | ND | ND | ND | ND | ND | ND | ND | ND | ND | ND | 0.06 |
|---|---|---|---|---|---|---|---|---|---|---|---|---|
| Total (% area) | 0 | 0.91 | 0 | 0.46 | 0 | 0.06 | 0 | 0.32 | 0.11 | 0.73 | 0.09 | 0.92 |

| Time | #6 | | #7 | | #8 | | #9 | |
|---|---|---|---|---|---|---|---|---|
| (m) | 0 | 6 | 0 | 6 | 0 | 6 | 0 | 6 |
| Assay | 100 | 99.3 | 100 | 99.6 | 100 | 98.2 | 100 | 101.8 |
| A | ND | 0.06 | ND | BQL | ND | 0.05 | ND | ND |
| B | ND | 0.17 | ND | 0.08 | ND | 0.2 | ND | BQL |
| D | ND | ND | ND | ND | ND | ND | ND | ND |
| G | ND | 0.07 | ND | ND | ND | 0.34 | ND | 0.4 |
| H | ND | 0.08 | ND | ND | ND | ND | ND | BQL |
| Bisalkyl-buprenorphine | ND | 0.05 | ND | ND | ND | ND | ND | ND |
| Unspecified | BQL | ND | 0.05 | 0.08 | 0.06 | 0.21 | ND | ND |
| Total (% area) | 0 | 0.43 | 0.05 | 0.16 | 0.06 | 0.8 | 0 | 0.4 |

BQL = Below Quantifiable Limit;
ND = Not Detected

Sublingual buprenorphine spray formulations contained less than one percent total impurities after six months at 40° C. Control and formulations 1, 3, 4, 5, 6, 8 and 9 showed significant increase in levels of individual impurities (impurity B, impurity G, bisalkyl or unspecified impurity) at the 6 month time point whereas formulations containing BHA and BHT (#2) or sodium thiosulfate (#7) showed good stability. pH also played a role in the stability of the product. These results represent sublingual buprenorphine spray formulations that would remain stable for two years at room temperature.

Example 2: Stable Buprenorphine/Naloxone Formulations

Method of Making the Formulations

Sublingual spray formulations were created by first degassing ethanol and USP purified water, separately. Next, the ethanol and purified water were each purged with nitrogen. Soluble excipients were then dissolved in either the ethanol or the purified water based on their solubility. Next, the solutions were combined. Buprenorphine and naloxone were added to the final solution and mixed until dissolved.

Formulations

TABLE 3

Stable Buprenorphine/Naloxone Sublingual Spray Formulations

| Formulation | Control #2 | #10 | #11 | #12 | #13 |
|---|---|---|---|---|---|
| Buprenorphine HCl | 8.602 | 8.602 | 8.602 | 8.602 | 8.602 |
| Naloxone HCl | 2.44 | 2.44 | 2.44 | 2.44 | 2.44 |
| Water (USP) | 28.958 | 28.9455 | 28.943 | 28.938 | 28.933 |
| Ethanol | 55 | 55 | 55 | 55 | 55 |
| Propylene Glycol | 5 | 5 | 5 | 5 | 5 |
| BHA | | | | 0.01 | |
| BHT | | | | 0.005 | |
| Sodium Ascorbate | | | | | 0.02 |
| Sodium Thiosulfate | | 0.01 | 0.01 | | |
| Citric Acid | | 0.0025 | | | |
| Disodium Edetate | | | 0.005 | 0.005 | 0.005 | values = % w/w

Stability Data

The formulations listed in Table 3 were subject to stability test at 40° C.±2° C. under 75%±5% relative humidity for three months and at ±25° C. under 60%±5% relative humidity for three months. Stability data was collected at zero, one, two and three months at 40° C. and at zero, one and three months at 25° C. Assay and impurities were detected using high performance liquid chromatography with an ultraviolet detector. Buprenorphine assay was performed at 288 nm and indicated as a % of initial concentration. For all buprenorphine impurities, analysis was performed at 240 nm and expressed as a % area. Naloxone assay was performed at 280 nm and indicated as a % of initial concentration and for all naloxone impurities, analysis was performed at 230 nm. Amounts of particular impurities are listed in Tables 4 and 5 for 40° C. and in Table 6 for 25° C. as a percentage of the area of each formulation along with amount of total impurities. Relative retention time ("RRT") is given for each impurity.

TABLE 4

Stability Data for Control #2 stored at 40° C. ± 2° C./75% ± 5% relative humidity for 1, 2 and 3 months.

| 40° C. | | Control #2 | | | | 40° C. | | Control #2 | | | |
|---|---|---|---|---|---|---|---|---|---|---|---|
| Buprenorphine | RRT | 0 m | 1 m | 2 m | 3 m | Naloxone | RRT | 0 m | 1 m | 2 m | 3 m |
| Assay | | 100% | 96.93% | 94.22% | 94.27% | Assay | | 100% | 96.31% | 97.22% | 95.62% |
| Impurity B | 0.4 | ND | ND | 0.09% | 0.12% | Impurity C | 0.66 | ND | 1.11% | 1.71% | 2.02% |
| Impurity J | 1.1 | ND | ND | BQL | BQL | Impurity A | 0.83 | ND | ND | 0.10% | 0.19% |
| Impurity F | 1.27 | ND | ND | BQL | BQL | Impurity E | 2.85 | ND | ND | 0.09% | ND |
| Impurity G | 1.8 | 0.11% | 1.84% | 3.10% | 4.14% | Impurity D | 0.20 | ND | ND | ND | 0.09% |
| Unknown | 0.26 | ND | ND | ND | BQL | Unknown | 0.28 | ND | 0.09% | 0.17% | 0.23% |

TABLE 4-continued

Stability Data for Control #2 stored at 40° C. ± 2° C./75% ± 5% relative humidity for 1, 2 and 3 months.

| 40° C. Buprenorphine | RRT | 0 m | 1 m | 2 m | 3 m | 40° C. Naloxone | RRT | 0 m | 1 m | 2 m | 3 m |
|---|---|---|---|---|---|---|---|---|---|---|---|
| Impurities | 0.86 | ND | 0.28% | 0.46% | 0.63% | Impurities | 0.30 | ND | ND | 0.09% | 0.17% |
|  | 2.15 | ND | 0.23% | 0.33% | 0.42% |  | 0.47 | ND | ND | ND | 0.06% |
| Total (% area) |  | 0.11% | 2.35% | 3.98% | 5.31% |  | 0.52 | ND | 0.34% | 0.73% | 1.17% |
|  |  |  |  |  |  |  | 4.30 | ND | ND | ND | 0.33% |
|  |  |  |  |  |  | Total (% area) |  | 0.00% | 1.54% | 2.89% | 4.26% |

BQL = Below Qantifiable Limit;
ND = Not Detected

The control formulation for the buprenorphine/naloxone sublingual spray formulation contained greater than 1% impurities of both buprenorphine and naloxone within one month at 40° C. and between about 4% and about 5% at three months.

TABLE 5

Stability Data for Buprenorphine/Naloxone Sublingual Spray Formulations stored at 40° C. ± 2° C./75% ± 5% relative humidity for 1, 2 and 3 months.

| 40° C. Buprenorphine | RRT | #10 0 m | 1 m | 2 m | 3 m | RRT | #11 0 m | 1 m | 2 m | 3 m |
|---|---|---|---|---|---|---|---|---|---|---|
| Assay |  | 100% | 98.72% | 96.90% | 100.06% |  | 100% | 99.26% | 98.91% | 99.96% |
| Impurity G |  |  |  |  |  |  |  |  |  |  |
| Total (% area) |  | 0.00% | 0.00% | 0.00% | 0.00% |  | 0.00% | 0.00% | 0.00% | 0.00% |

| Naloxone | RRT | 0 m | 1 m | 2 m | 3 m | RRT | 0 m | 1 m | 2 m | 3 m |
|---|---|---|---|---|---|---|---|---|---|---|
| Assay |  | 100% | 99.19% | 102.69% | 102.42% |  | 100% | 99.84% | 102.75% | 102.00% |
| Impurity C |  |  |  |  |  |  |  |  |  |  |
| Unknown Impurities |  |  |  |  |  |  |  |  |  |  |
| Total (% area) |  | 0.00% | 0.00% | 0.00% | 0.00% |  | 0.00% | 0.00% | 0.00% | 0.00% |

| 40° C. Buprenorphine | RRT | #12 0 m | 1 m | 2 m | 3 m | RRT | #13 0 m | 1 m | 2 m | 3 m |
|---|---|---|---|---|---|---|---|---|---|---|
| Assay |  | 100 | 99.50% | 101.44% | 101.22% |  | 100% | 99.06% | 100.30% | 99.36% |
| Impurity G | 1.8 | ND | ND | ND | 0.05% |  |  |  |  |  |
| Total (% area) |  | 0.00% | 0.00% | 0.00% | 0.05% |  | 0.00% | 0.00% | 0.00% | 0.00% |

| Naloxone | RRT | 0 m | 1 m | 2 m | 3 m | RRT | 0 m | 1 m | 2 m | 3 m |
|---|---|---|---|---|---|---|---|---|---|---|
| Assay |  | 100% | 97.91% | 102.36% | 103.11% |  | 100% | 101.42% | 102.72% | 103.38% |
| Impurity C | 0.66 | ND | ND | 0.11% | 0.14% | 0.66 | ND | ND | ND | 0.09% |
| Unknown | 0.52 | ND | ND | 0.07% | 0.12% | 0.52 | ND | ND | BQL | ND |
| Impurities | 4.02 | ND | ND | ND | ND |  |  |  |  |  |
| Total (% area) |  | 0.00% | 0.00% | 0.18% | 0.26% |  | 0.00% | 0.00% | 0.00% | 0.09% |

BQL = Below Qantifiable Limit;
ND = Not Detected

All formulations had less than 1% total impurities at three months. Similar to the buprenorphine only formulations in Example 1, formulations containing sodium thiosulfate (#10 and #11) were exceptionally stable with no impurities after three months. Formulation #12 contains BHA and BHT as the antioxidant and had significant impurities of naloxone (0.26% total impurities). Formulation #13 contains sodium ascorbate and had no impurities of buprenorphine and 0.09% total impurities of naloxone. These results represent sublingual spray formulations that would remain stable for one year at room temperature.

TABLE 6

Stability Data for Buprenorphine/Naloxone Sublingual Spray Formulations stored
at 25° C. ± 2° C./60% ± 5% relative humidity for 1, 2 and 3 months.

| 25° C. | | Control #2 | | | | #10 | | | | #11 | | |
|---|---|---|---|---|---|---|---|---|---|---|---|---|
| Buprenorphine | RRT | 0 m | 1 m | 3 m | RRT | 0 m | 1 m | 3 m | RRT | 0 m | 1 m | 3 m |
| Assay | | 100% | 97.33% | 98.25% | | 100% | 100.14% | 98.82% | | 100% | 100.01% | 99.80% |
| Impurity G | 1.8 | 0.11% | 0.44% | 1.08% | | | | | | | | |
| Unknown | 0.86 | ND | ND | 0.13% | | | | | | | | |
| Impurities | 1.8 | ND | ND | 0.09% | | | | | | | | |
| Total (% area) | | 0.11% | 0.44% | 1.30% | | 0.00% | 0.00% | 0.00% | | 0.00% | 0.00% | 0.00% |
| Naloxone | RRT | 0 m | 1 m | 3 m | RRT | 0 m | 1 m | 3 m | RRT | 0 m | 1 m | 3 m |
| Assay | | 100% | 98.56% | 100.00% | | 100% | 99.08% | 101.67% | | 100% | 99.03% | 102.16% |
| Impurity C | 0.66 | ND | 0.41% | 0.97% | | | | | | | | |
| Impurity A | | | | | | | | | | | | |
| Unknown | 0.28 | ND | ND | 0.08% | | | | | | | | |
| Impurities | 0.52 | ND | ND | 0.13% | | | | | | | | |
| Total (% area) | | 0.00% | 0.41% | 1.18% | | 0.93% | 0.00% | 0.00% | | 0.00% | 0.00% | 0.00% |

| 25° C. | | #12 | | | | #13 | | |
|---|---|---|---|---|---|---|---|---|
| Buprenorphine | RRT | 0 m | 1 m | 3 m | RRT | 0 m | 1 m | 3 m |
| Assay | | 100 | 101.29% | 100.14% | | 100% | 98.37% | 99.74% |
| Impurity G | | | | | | | | |
| Unknown | | | | | | | | |
| Impurities | | | | | | | | |
| Total (% area) | | 0.00% | 0.00% | 0.00% | | 0.00% | 0.00% | 0.00% |
| Naloxone | RRT | 0 m | 1 m | 3 m | RRT | 0 m | 1 m | 3 m |
| Assay | | 100% | 99.03% | 101.77% | | 100% | 100.65% | 102.67% |
| Impurity C | | | | | | | | |
| Impurity A | | | | | 0.83 | ND | ND | 0.11% |
| Unknown | | | | | | | | |
| Impurities | | | | | 0.52 | ND | ND | BQL |
| Total (% area) | | 0.00% | 0.00% | 0.00% | | 0.00% | 0.00% | 0.11% |

BQL = Below Qantifiable Limit;
ND = Not Detected

The control formulation had greater than 1% impurities at three months. All formulations containing antioxidants had less than 1% total impurities at three months. Similar to the buprenorphine only formulations in Example 1, formulations containing sodium thiosulfate (#10 and #11) or a mixture of BHA and BHT (#12) were exceptionally stable with no impurities after three months. Formulation #13 which contains sodium ascorbate had no impurities of buprenorphine and 0.11% total impurities of naloxone after storage at 25° C.±2° C./75%±5% relative humidity.

Example 3: Pharmacokinetics of Buprenorphine Sublingual Spray Formulations

A study was designed and executed to determine the pharmacokinetics of buprenorphine sublingual spray formulations of the present invention after administration in healthy volunteers under fasting conditions.

The study was a single center, single dose, open-label, 1-sequence, 2-period, ascending dose study design in twelve healthy male and female subjects. The following dose levels of the investigational product were administered under fasting conditions: Dose 1: A single 0.5 mg dose (1 spray of 100 microliters) of Buprenorphine 5 mg/mL Sublingual Spray; and Dose 2: A single 1.0 mg dose (2 sprays of 100 microliters) of Buprenorphine 5 mg/mL Sublingual Spray.

The subjects arrived at the clinical site more than 10 hours before the buprenorphine administration. The subjected were supervised overnight (while fasting) and a single 50 mg dose of naltrexone (1×50 mg tablet) was orally administered with 240 mL of water approximately 1 hour prior to the buprenorphine administration to provide blockade of the pharmacological effects of buprenorphine. Then, a single dose (0.5 mg in period 1 and 1.0 mg in period 2) of the buprenorphine formulation was sublingually administered in the morning. Subjects were allowed to leave the clinical site after the 24-hour post-dose blood draw and returned to the clinical site before the remaining blood sample. The second dose level was administered following favorable safety review. The buprenorphine administrations were separated by a wash-out of 14 calendar days. The parameters are summarized below in Table 7.

TABLE 7

Summary of Pharmacokinetic Parameters

| | Buprenorphine 0.5 mg | | Buprenorphine 1 mg | |
|---|---|---|---|---|
| Parameter | MEAN | C.V. | MEAN | C.V. |
| $C_{max}$ (ng/mL) | 0.761 | 19.0 | 1.38 | 10.2 |
| $ln(C_{max})$ | −0.2904 | −67.1 | 0.3169 | 31.2 |
| $T_{max}$ (hours) * | 1.75 | 30.8 | 1.50 | 30.6 |
| $AUC_{0-T}$ (ng · h/mL) | 4.37 | 13.6 | 9.12 | 10.7 |
| $ln(AUC_{0-T})$ | 1.4671 | 9.0 | 2.2053 | 5.0 |
| $AUC_{0-\infty}$ (ng · h/mL) | 4.81 | 13.3 | 10.2 | 10.6 |
| $ln(AUC_{0-\infty})$ | 1.5614 | 8.7 | 2.3170 | 4.7 |
| $AUC_{0-T/\infty}$ (%) | 91.19 | 6.6 | 89.49 | 3.5 |
| $\lambda_Z$ (hours$^{-1}$) | 0.0959 | 53.3 | 0.0313 | 17.0 |
| $T_{half}$ (hours) | 9.75 | 57.4 | 22.87 | 20.1 |
| $V_D/F$ (L) | 1450 | 54.9 | 3250 | 19.4 |
| Cl/F (L/h) | 106 | 13.8 | 99.1 | 11.2 |
| $C_{max}/D$ (ng/mL) | 0.761 | 19.0 | 0.690 | 10.2 |
| $ln(C_{max}/D)$ | −0.2904 | −67.1 | −0.3763 | −26.3 |
| $AUC_{0-T}/D$ (ng · h/mL) | 4.37 | 13.6 | 4.56 | 10.7 |
| $ln(AUC_{0-T}/D)$ | 1.4671 | 9.0 | 1.5122 | 7.3 |
| $AUC_{0-\infty}/D$ (ng · h/mL) | 4.81 | 13.3 | 5.10 | 10.6 |
| $ln(AUC_{0-\infty}/D)$ | 1.5614 | 8.7 | 1.6238 | 6.7 |

* $T_{max}$, the median is presented

As seen in Table 7, the Cmax obtained for buprenorphine were 0.761 ng/mL and 1.38 ng/mL. The Tmax observed for buprenorphine was 1.75 and 1.50 hours following the ascending doses.

Example 4: Bioavailability of Buprenorphine

A study was designed and executed in order to compare the rate and extent of absorption and bioavailability of 1 mg buprenorphine sublingual spray formulations of the present invention with 0.3 mg (1 mL) Buprenex® (buprenorphine HCl) intramuscular injection and 0.3 mg (1 mL) Buprenex® (buprenorphine HCl) intravenous bolus injection.

This was an open-label, 3-treatment, 3-period, 6-sequence, single-dose, randomized crossover study. Eighteen healthy male and female volunteers were randomly assigned to 1 of 6 treatment sequences. Dosing occurred after an overnight fast and there was a minimum 14-day washout between the dosing in two periods. Blood samples for the measurement of the plasma concentrations of buprenorphine were collected before (pre-dose) and at 5, 10, 20, 30, and 40 minutes and at 1, 1.25, 1.5, 2, 4, 6, 8, 10, 12, 16, 24, 36, 48, 72, 96, 120, and 144 hours after dosing. The results of this study are summarized below in Table 8.

TABLE 8

Bioavailability of Buprenorphine

| Parameter* | Sublingual Spray 1 mg | Intramuscular 0.3 mg | Intravenous 0.3 mg |
|---|---|---|---|
| Cmax (ng/mL) | 1.20 ± 0.507 (18) | 1.73 ± 1.08 (18) | 3.95 ± 3.66 (18) |
| Tmax (h) | 1.50 (18) [0.50-2.00] | 0.17 (18) [0.083-1.50] | 0.083 (18) [0.083-0.333] |
| AUC(0-t) (h × ng/mL) | 7.31 ± 2.80 (18) | 4.97 ± 0.90 (18) | 5.09 ± 1.01 (18) |
| AUC(inf) (h × ng/mL) | 8.19 ± 3.27 (15) | 5.50 ± 0.83 (15) | 5.51 ± 1.21 (17) |
| λz (l/h) | 0.0551 ± 0.0357 (15) | 0.0655 ± 0.0210 (15) | 0.1028 ± 0.0641 (17) |
| t½ (h) | 17.1 ± 8.62 (15) | 12.0 ± 5.31 (15) | 9.37 ± 6.49 (17) |

The absolute bioavailability of buprenorphine, based on AUC(0-t) and AUC(inf), after sublingual administration was 41.03% and 42.57%, respectively.

Example 5: Buprenorphine Spray Droplet Size Distribution, Spray Pattern and Plume Geometry A challenge of creating a buprenorphine sublingual spray formulation is that it must be capable of producing spray droplets that are over 10 microns in diameter. Spray droplets 10 microns or smaller could be inhaled into the lungs. The optimal particle size for sublingual spray droplets is from 20 to about 200 microns in diameter. It is desirable for the formulation to have droplet sizes near 20 because this increases the surface area and increased surface area exposure is one factor that contributes to a high bioavailability. Sublingual formulations should be able to maintain a consistent droplet size throughout its shelf life. Applicants found during testing that formulations of the present invention yielded desirable droplet sizes for sublingual administration. The testing also revealed that the formulation dose remains consistent when administered with a spray pump.

Five milligram per mL buprenorphine spray formulations of the present invention were subjected to two different storage conditions (25 and 40 degrees C.) and samples were taken at two different times (5M and 6M) for spray droplet size distribution analysis. Droplet analysis was conducted using standard laser analysis procedures known by those of skill in the art.

Droplet size distribution (Dv10, Dv50, Dv90, percent droplets less than 10 micrometers in diameter, D(4,3) and Span tested at two distances, 3 cm and 6 cm for upright and horizontal samples stored at 25 and 40 degrees C.) and spray pattern (Dmin, Dmax and ovality ratio tested at two distances, 3 cm and 6 cm for upright and horizontal samples stored at 25 and 40 degrees C.) were determined. D(4,3) refers to the volume moment mean of the particles; Dv10 refers to droplet size for which 10% of the total volume is obtained; Dv50 refers to droplet size for which 50% of the total volume is obtained; Dv90 refers to droplet size for which 90% of the total volume is obtained; Span refers to distribution span (Dv90−Dv10)/Dv50; DSD refers to droplet size distribution; the temperature listed is the storage temperature; U refers to an upright position of the spray pump; and H refers to horizontal position of the spray pump. The results of these studies can be seen below in Tables 9 to 40.

In addition, the formulations were tested for plume geometry including width and angle using standard procedures known by those of skill in the art. This testing showed that the spray pattern and plume were acceptable for formulations of the present invention. The results of these studies can be seen below in Tables 41 and 42.

TABLE 9

Droplet Size Distribution at 3 cm for sample stored
at 25 degrees C., Upright position, 5 M

| | DSD 3 cm 25° C. - U | Dv(10) (μm) | Dv(50) (μm) | Dv(90) (μm) | % <10μ | D(4,3) (μm) | Span |
|---|---|---|---|---|---|---|---|
| Range | Mean | 25.37 | 53.25 | 111.1 | 0.9507 | 62.07 | 1.609 |
| | Min | 24.38 | 51.44 | 106.0 | 0.8534 | 59.51 | 1.539 |
| | Max | 26.20 | 55.85 | 119.4 | 1.0410 | 65.72 | 1.705 |

TABLE 10

Droplet Size Distribution at 6 cm for sample stored
at 25 degrees C., Upright position, 5 M

| | DSD 6 cm 25° C. - U | Dv(10) (μm) | Dv(50) (μm) | Dv(90) (μm) | % <10μ | D(4,3) (μm) | Span |
|---|---|---|---|---|---|---|---|
| Range | Mean | 30.58 | 56.68 | 102.7 | 1.5794 | 62.37 | 1.270 |
| | Min | 28.93 | 52.00 | 90.5 | 1.4610 | 56.45 | 1.171 |
| | Max | 31.60 | 60.47 | 113.4 | 1.7840 | 67.41 | 1.355 |

TABLE 11

Droplet Size Distribution at 3 cm for sample stored
at 25 degrees C., Horizontal position, 5 M

| | DSD 3 cm 25° C. - H | Dv(10) (μm) | Dv(50) (μm) | Dv(90) (μm) | % <10μ | D(4,3) (μm) | Span |
|---|---|---|---|---|---|---|---|
| Range | Mean | 24.65 | 53.78 | 138.2 | 0.7813 | 72.37 | 2.123 |
| | Min | 21.87 | 50.76 | 105.8 | 0.0000 | 59.42 | 1.593 |
| | Max | 26.70 | 58.10 | 194.5 | 1.1560 | 89.39 | 3.295 |

TABLE 12

Droplet Size Distribution at 6 cm for sample stored
at 25 degrees C., Horizontal position, 5 M

| | DSD 6 cm 25° C. - H | Dv(10) (μm) | Dv(50) (μm) | Dv(90) (μm) | % <10μ | D(4,3) (μm) | Span |
|---|---|---|---|---|---|---|---|
| Range | Mean | 30.18 | 55.86 | 108.3 | 0.8612 | 68.69 | 1.403 |
| | Min | 26.86 | 52.98 | 96.1 | 0.0637 | 63.28 | 1.171 |
| | Max | 32.03 | 59.90 | 124.7 | 1.6630 | 74.75 | 1.782 |

TABLE 13

Droplet Size Distribution at 3 cm for sample stored
at 40 degrees C., Upright position, 5 M

| | DSD 3 cm 40° C. - U | Dv(10) (μm) | Dv(50) (μm) | Dv(90) (μm) | % <10μ | D(4,3) (μm) | Span |
|---|---|---|---|---|---|---|---|
| Range | Mean | 26.75 | 56.64 | 120.3 | 0.9120 | 66.53 | 1.651 |
| | Min | 26.22 | 55.44 | 116.8 | 0.7907 | 65.09 | 1.612 |
| | Max | 27.33 | 58.02 | 122.7 | 0.9900 | 67.94 | 1.689 |

TABLE 14

Droplet Size Distribution at 6 cm for sample stored
at 40 degrees C., Upright position, 5 M

| | DSD 6 cm 40° C. - U | Dv(10) (μm) | Dv(50) (μm) | Dv(90) (μm) | % <10μ | D(4,3) (μm) | Span |
|---|---|---|---|---|---|---|---|
| Range | Mean | 32.87 | 63.39 | 121.7 | 1.3128 | 71.44 | 1.390 |
| | Min | 31.62 | 59.93 | 111.7 | 0.6002 | 66.68 | 1.280 |
| | Max | 35.85 | 79.44 | 174.7 | 1.5100 | 94.26 | 1.748 |

TABLE 15

Droplet Size Distribution at 3 cm for sample stored
at 40 degrees C., Horizontal position, 5 M

| | DSD 3 cm 40° C. - H | Dv(10) (μm) | Dv(50) (μm) | Dv(90) (μm) | % <10μ | D(4,3) (μm) | Span |
|---|---|---|---|---|---|---|---|
| Range | Mean | 26.08 | 55.51 | 116.1 | 0.8906 | 64.59 | 1.619 |
| | Min | 24.86 | 51.65 | 104.2 | 0.7230 | 59.27 | 1.530 |
| | Max | 27.12 | 58.59 | 126.6 | 1.0880 | 69.05 | 1.710 |

TABLE 16

Droplet Size Distribution at 6 cm for sample stored
at 40 degrees C., Horizontal position, 5 M

| | DSD 6 cm 40° C. - H | Dv(10) (μm) | Dv(50) (μm) | Dv(90) (μm) | % <10μ | D(4,3) (μm) | Span |
|---|---|---|---|---|---|---|---|
| Range | Mean | 30.96 | 57.88 | 105.6 | 1.5678 | 63.84 | 1.288 |
| | Min | 29.43 | 54.51 | 97.5 | 1.1350 | 59.57 | 1.195 |
| | Max | 31.84 | 62.23 | 120.3 | 1.7230 | 70.09 | 1.429 |

TABLE 17

Plume Geometry at 3 cm for sample stored
at 40 degrees C., Upright position, 5 M

| | Spray Pattern 3 cm 40° C. - U | Dmin (mm) | Dmax (mm) | Ovality Ratio |
|---|---|---|---|---|
| Range | Mean | 12.8 | 20.0 | 1.584 |
| | Min | 11.6 | 17.2 | 1.289 |
| | Max | 13.6 | 24.7 | 2.043 |

TABLE 18

Plume Geometry at 6 cm for sample stored at
25 degrees C., Horizontal position, 5 M

| | Spray Pattern 6 cm 25° C. - H | Dmin (mm) | Dmax (mm) | Ovality Ratio |
|---|---|---|---|---|
| Range | Mean | 21.4 | 29.1 | 1.362 |
| | Min | 20.2 | 27.1 | 1.228 |
| | Max | 22.5 | 32.0 | 1.511 |

TABLE 19

Plume Geometry at 3 cm for sample stored at
25 degrees C., Horizontal position, 5 M

| | Spray Pattern 3 cm 25° C. - H | Dmin (mm) | Dmax (mm) | Ovality Ratio |
|---|---|---|---|---|
| Range | Mean | 13.6 | 19.5 | 1.436 |
| | Min | 13.0 | 18.0 | 1.382 |
| | Max | 14.2 | 21.1 | 1.580 |

TABLE 20

Plume Geometry at 6 cm for sample stored
at 25 degrees C., Upright position, 5 M

| | Spray Pattern 6 cm 25° C. - U | Dmin (mm) | Dmax (mm) | Ovality Ratio |
|---|---|---|---|---|
| Range | Mean | 21.3 | 30.1 | 1.421 |
| | Min | 19.9 | 26.7 | 1.244 |
| | Max | 22.3 | 33.4 | 1.679 |

TABLE 21

Plume Geometry at 3 cm for sample stored
at 25 degrees C., Upright position, 5 M

| | Spray Pattern 3 cm 25° C. - U | Dmin (mm) | Dmax (mm) | Ovality Ratio |
|---|---|---|---|---|
| Range | Mean | 14.4 | 19.1 | 1.320 |
| | Min | 13.2 | 17.1 | 1.212 |
| | Max | 15.9 | 22.3 | 1.426 |

TABLE 22

Plume Geometry at 3 cm for sample stored at
40 degrees C., Horizontal position, 5 M

| | Spray Pattern 3 cm 40° C. - H | Dmin (mm) | Dmax (mm) | Ovality Ratio |
|---|---|---|---|---|
| Range | Mean | 13.0 | 18.3 | 1.415 |
| | Min | 12.3 | 16.1 | 1.180 |
| | Max | 13.9 | 21.3 | 1.662 |

TABLE 23

Plume Geometry at 6 cm for sample stored
at 40 degrees C., Upright position, 5 M

| | Spray Pattern 6 cm 40° C. - U | Dmin (mm) | Dmax (mm) | Ovality Ratio |
|---|---|---|---|---|
| Range | Mean | 20.8 | 32.2 | 1.578 |
| | Min | 18.3 | 25.3 | 1.151 |
| | Max | 22.2 | 43.2 | 2.317 |

TABLE 24

Plume Geometry at 6 cm for sample stored at
40 degrees C., Horizontal position, 5 M

| | Spray Pattern 6 cm 40° C. - H | Dmin (mm) | Dmax (mm) | Ovality Ratio |
|---|---|---|---|---|
| Range | Mean | 21.5 | 29.4 | 1.371 |
| | Min | 19.8 | 27.1 | 1.253 |
| | Max | 23.3 | 32.5 | 1.639 |

TABLE 25

Droplet Size Distribution at 3 cm for sample stored
at 25 degrees C., Upright position, 6 M

|  | DSD 3 cm 25° C. - U | Dv(10) (μm) | Dv(50) (μm) | Dv(90) (μm) | % <10μ | D(4,3) (μm) | Span |
|---|---|---|---|---|---|---|---|
|  | Mean | 26.22 | 57.53 | 121.8 | 0.5523 | 67.25 | 1.652 |
| Range | Min | 24.63 | 50.98 | 104.4 | 0.0000 | 59.18 | 1.544 |
|  | Max | 27.73 | 68.01 | 148.6 | 0.9883 | 79.42 | 1.783 |

TABLE 26

Droplet Size Distribution at 6 cm for sample stored
at 25 degrees C., Upright position, 6 M

|  | DSD 6 cm 25° C. - U | Dv(10) (μm) | Dv(50) (μm) | Dv(90) (μm) | % <10μ | D(4,3) (μm) | Span |
|---|---|---|---|---|---|---|---|
|  | Mean | 31.87 | 62.59 | 119.9 | 1.1915 | 70.21 | 1.405 |
| Range | Min | 29.24 | 58.74 | 111.6 | 0.8993 | 65.79 | 1.282 |
|  | Max | 33.93 | 66.29 | 133.7 | 1.4090 | 75.92 | 1.528 |

TABLE 27

Droplet Size Distribution at 3 cm for sample stored
at 25 degrees C., Horizontal position, 6 M

|  | DSD 3 cm 25° C. - H | Dv(10) (μm) | Dv(50) (μm) | Dv(90) (μm) | % <10μ | D(4,3) (μm) | Span |
|---|---|---|---|---|---|---|---|
|  | Mean | 24.55 | 50.03 | 101.6 | 0.8918 | 57.62 | 1.538 |
| Range | Min | 22.88 | 46.53 | 91.7 | 0.0000 | 52.75 | 1.476 |
|  | Max | 25.64 | 52.39 | 109.5 | 1.3350 | 61.24 | 1.633 |

TABLE 28

Droplet Size Distribution at 6 cm for sample stored
at 25 degrees C., Horizontal position, 6 M

|  | DSD 6 cm 25° C. - H | Dv(10) (μm) | Dv(50) (μm) | Dv(90) (μm) | % <10μ | D(4,3) (μm) | Span |
|---|---|---|---|---|---|---|---|
|  | Mean | 29.58 | 56.85 | 105.2 | 1.3818 | 62.82 | 1.323 |
| Range | Min | 28.53 | 51.57 | 89.4 | 1.0870 | 55.73 | 1.178 |
|  | Max | 30.75 | 60.69 | 116.4 | 1.6780 | 67.86 | 1.434 |

TABLE 29

Droplet Size Distribution at 3 cm for sample stored
at 40 degrees C., Upright position, 6 M

|  | DSD 3 cm 40° C. - U | Dv(10) (μm) | Dv(50) (μm) | Dv(90) (μm) | % <10μ | D(4,3) (μm) | Span |
|---|---|---|---|---|---|---|---|
|  | Mean | 27.60 | 58.79 | 125.9 | 0.4862 | 69.31 | 1.669 |
| Range | Min | 26.50 | 52.85 | 111.3 | 0.0000 | 62.36 | 1.579 |
|  | Max | 29.11 | 65.51 | 140.0 | 0.7686 | 76.44 | 1.729 |

TABLE 30

Droplet Size Distribution at 6 cm for sample stored
at 40 degrees C., Upright position, 6 M

|  | DSD 6 cm 40° C. - U | Dv(10) (μm) | Dv(50) (μm) | Dv(90) (μm) | % <10μ | D(4,3) (μm) | Span |
|---|---|---|---|---|---|---|---|
|  | Mean | 33.68 | 67.20 | 131.3 | 1.0200 | 76.03 | 1.450 |
| Range | Min | 32.54 | 63.80 | 118.0 | 0.8835 | 70.69 | 1.314 |
|  | Max | 35.01 | 70.75 | 141.2 | 1.4480 | 80.26 | 1.543 |

TABLE 31

Droplet Size Distribution at 3 cm for sample stored
at 40 degrees C., Horizontal position, 6 M

| | DSD 3 cm 40° C. - H | Dv(10) (μm) | Dv(50) (μm) | Dv(90) (μm) | % <10μ | D(4,3) (μm) | Span |
|---|---|---|---|---|---|---|---|
| Range | Mean | 27.75 | 55.42 | 114.3 | 0.0005 | 64.60 | 1.559 |
| | Min | 26.47 | 52.01 | 104.6 | 0.0000 | 60.13 | 1.475 |
| | Max | 29.22 | 59.01 | 124.9 | 0.0019 | 69.62 | 1.621 |

TABLE 32

Droplet Size Distribution at 6 cm for sample stored
at 40 degrees C., Horizontal position, 6 M

| | DSD 6 cm 40° C. - H | Dv(10) (μm) | Dv(50) (μm) | Dv(90) (μm) | % <10μ | D(4,3) (μm) | Span |
|---|---|---|---|---|---|---|---|
| Range | Mean | 34.33 | 63.86 | 118.0 | 0.9685 | 70.95 | 1.309 |
| | Min | 32.47 | 60.19 | 110.1 | 0.0624 | 66.54 | 1.251 |
| | Max | 37.21 | 68.17 | 129.6 | 1.5090 | 76.88 | 1.363 |

TABLE 33

Plume Geometry at 3 cm for sample stored
at 25 degrees C., Upright position, 6 M

| | Spray Pattern 3 cm 25° C. - U | Dmin (mm) | Dmax (mm) | Ovality Ratio |
|---|---|---|---|---|
| Range | Mean | 14.0 | 20.8 | 1.489 |
| | Min | 13.4 | 17.9 | 1.300 |
| | Max | 14.5 | 23.1 | 1.664 |

TABLE 34

Plume Geometry at 6 cm for sample stored
at 25 degrees C., Upright position, 6 M

| | Spray Pattern 6 cm 25° C. - U | Dmin (mm) | Dmax (mm) | Ovality Ratio |
|---|---|---|---|---|
| Range | Mean | 20.3 | 30.3 | 1.497 |
| | Min | 19.1 | 27.4 | 1.320 |
| | Max | 21.1 | 33.6 | 1.705 |

TABLE 35

Plume Geometry at 3 cm for sample stored at
25 degrees C., Horizontal position, 6 M

| | Spray Pattern 3 cm 25° C. - H | Dmin (mm) | Dmax (mm) | Ovality Ratio |
|---|---|---|---|---|
| Range | Mean | 14.0 | 21.4 | 1.549 |
| | Min | 12.9 | 19.8 | 1.276 |
| | Max | 15.7 | 23.9 | 1.852 |

TABLE 36

Plume Geometry at 6 cm for sample stored at
25 degrees C., Horizontal position, 6 M

| | Spray Pattern 6 cm 25° C. - H | Dmin (mm) | Dmax (mm) | Ovality Ratio |
|---|---|---|---|---|
| Range | Mean | 20.2 | 32.3 | 1.599 |
| | Min | 18.8 | 28.4 | 1.390 |
| | Max | 21.3 | 37.7 | 1.808 |

TABLE 37

Plume Geometry at 3 cm for sample stored
at 40 degrees C., Upright position, 6 M

| | Spray Pattern 3 cm 40° C. - U | Dmin (mm) | Dmax (mm) | Ovality Ratio |
|---|---|---|---|---|
| Range | Mean | 14.9 | 19.2 | 1.284 |
| | Min | 13.8 | 17.3 | 1.155 |
| | Max | 15.5 | 20.8 | 1.399 |

TABLE 38

Plume Geometry at 6 cm for sample stored
at 40 degrees C., Upright position, 6 M

| | Spray Pattern 6 cm 40° C. - U | Dmin (mm) | Dmax (mm) | Ovality Ratio |
|---|---|---|---|---|
| Range | Mean | 21.3 | 27.5 | 1.296 |
| | Min | 19.8 | 26.5 | 1.194 |
| | Max | 22.8 | 29.3 | 1.427 |

TABLE 39

Plume Geometry at 3 cm for sample stored at
40 degrees C., Horizontal position, 6 M

| | Spray Pattern 3 cm 40° C. - H | Dmin (mm) | Dmax (mm) | Ovality Ratio |
|---|---|---|---|---|
| Range | Mean | 14.6 | 22.5 | 1.547 |
| | Min | 13.9 | 20.8 | 1.430 |
| | Max | 16.0 | 24.8 | 1.781 |

TABLE 40

Plume Geometry at 6 cm for sample stored at
40 degrees C., Horizontal position, 6 M

| | Spray Pattern 6 cm 40° C. - H | Dmin (mm) | Dmax (mm) | Ovality Ratio |
|---|---|---|---|---|
| Range | Mean | 21.5 | 29.4 | 1.371 |
| | Min | 19.8 | 27.1 | 1.253 |
| | Max | 23.3 | 32.5 | 1.639 |

TABLE 41

Plume Geometry at 3 cm (width and angle)

|  |  | 3 cm | Width (mm) | Angle (°) |
|---|---|---|---|---|
| Range |  | Mean | 27.9 | 49.9 |
|  |  | Min | 25.5 | 46.1 |
|  |  | Max | 30.8 | 54.3 |

TABLE 42

Plume Geometry at 6 cm (width and angle)

|  |  | 6 cm | Width (mm) | Angle (°) |
|---|---|---|---|---|
| Range |  | Mean | 40.2 | 37.0 |
|  |  | Min | 36.0 | 33.4 |
|  |  | Max | 43.9 | 40.2 |

Example 6: Further Buprenorphine Formulations

TABLE 43

Further Buprenorphine Formulations

| Formulation | #14 | #15 | #16 | #17 | #18 |
|---|---|---|---|---|---|
| Buprenorphine HCl | 0.0813 | 0.1625 | 0.325 | 0.65 | 1.3 |
| BHA | 0.01 | 0.01 | 0.01 | 0.01 | 0.01 |
| BHT | 0.005 | 0.005 | 0.005 | 0.005 | 0.005 |
| L-Menthol | 0.05 | 0.05 | 0.05 | 0.05 | 0.05 |
| Ethanol | 55 | 55 | 55 | 55 | 55 |
| Propylene Glycol | 5 | 5 | 5 | 5 | 5 |
| Purified Water | 39.8537 | 39.7725 | 39.61 | 39.285 | 38.635 |
| Citric Acid Anhydrous | QS to pH | QS to pH | QS to pH | QS to pH | QS to pH |
| Sodium Hydroxide | QS to pH | QS to pH | QS to pH | QS to pH | QS to pH |
| Nitrogen | Sparging/Overlay | Sparging/Overlay | Sparging/Overlay | Sparging/Overlay | Sparging/Overlay |

Formulations #15, #16 and #17 are used in the clinical trial listed as Example 8 for acute pain indication, whereas formulations #14, #15, #16, #17 and #18 will be used in chronic pain indication.
Formulations #14, #15, #16, #17 and #18 represent 0.0625 mg, 0.125 mg, 0.25 mg, 0.5 mg and 1 mg doses, respectively. (Equivalent to buprenorphine base).
Values = % w/w.

Buprenorphine formulations of Table 43 were all stable upon preparation.

Example 7: Further Buprenorphine/Naloxone Formulations

TABLE 44

Further Buprenorphine/Naloxone Formulations

| Formulation | #19 | #20 | #21 | #22 | #23 | #24 | #25 |
|---|---|---|---|---|---|---|---|
| Buprenorphine HCl | 8.39 | 7.68 | 2.84 | 1.42 | 5.70 | 3.75 | 1.04 |
| NaloxoneHCl Dihydrate | 2.37 | 2.19 | 0.80 | 0.40 | 1.61 | 1.06 | 0.29 |
| L-Menthol | 0.05 | 0.05 | 0.05 | 0.05 | 0.05 | 0.05 | 0.05 |
| Edetate Disodium Dihydrate | 0.005 | 0.005 | 0.005 | 0.005 | 0.005 | 0.005 | 0.005 |
| Sodium Ascorbate | 0.02 | 0.02 | 0.02 | 0.02 | 0.02 | 0.02 | 0.02 |
| Ethanol | 55 | 55 | 55 | 55 | 55 | 55 | 55 |
| Propylene Glycol | 5 | 5 | 5 | 5 | 5 | 5 | 5 |
| Water | 29.165 | 30.059 | 36.281 | 38.103 | 32.614 | 35.114 | 38.596 |

Values = % w/w.

Buprenorphine/naloxone formulations of Table 44 were all stable upon preparation.

Example 8: Method of Treatment of Pain Using Buprenorphine

Specifications of the Study

This was a multicenter, randomized, double-blind, multiple-dose, placebo-controlled study evaluating the efficacy and safety of three dosing regimens of Buprenorphine Sublingual Spray (0.5 mg (formulation #17) three times daily ("tid"), 0.25 mg (formulation #16) tid, or 0.125 mg (formulation #15) tid), and/or matching placebo in subjects with moderate to severe postoperative pain after bunionectomy. 322 subjects were randomized. 298 subjects completed the study, and 24 discontinued for various reasons (9 to lack of efficacy; 14 due to nausea and emesis; and 1 for non-related hypotension); and one lost to follow-up.

The study lasted four months and comprised 4 periods: The Screening Period (Days −28 to −1), the Surgical Period (Day 0), the Treatment Period (48 hours; Days 1 to 3) and the Follow-up Period (Days 5 to 9).

The measurements of pain intensity and pain relied were conducted at Time 0 (i.e., at 5, 15, 30, and 45 minutes, and 1, 1.5, 2, 3, 4, 5, 6, 7, 8, 12, 16, 20, 24, 32, 40, and 48 hours).

As agreed with the U.S. Food and Drug Administration ("FDA"), the primary efficacy endpoint in this study was the Summed Pain Intensity Difference relative to baseline over a period of 48 hours (SPID-48). The patient assessment of pain intensity utilized a numeric pain scale (11-point scale with 0=no pain to 10=worst possible pain).

The secondary variables were as follows:
SPID over 0 to 4 hours (SPID-4), over 0 to 8 hours (SPID-8), and over 0 to 24 hours (SPID-24) after Time 0;
Time to onset of analgesia (measured as time to perceptible pain relief confirmed by meaningful pain relief using the 2-stopwatch method); and
Pain intensity difference (PID) at each scheduled time point after Time 0.

The disposition of subjects is depicted in the flow chart in FIG. 1.

Results

The primary efficacy endpoint was statistically significant at all doses studied. The Buprenorphine Sublingual Spray 0.5 mg tid demonstrated the largest reduction in SPID-48 and was statistically significant to placebo (p<0.0001). The 0.25 mg tid and 0.125 mg tid doses also demonstrated statistically significant reductions in SPID-48 (p=0.0108 and p=0.0120, respectively). All treatments were generally well tolerated.

Figure 2:
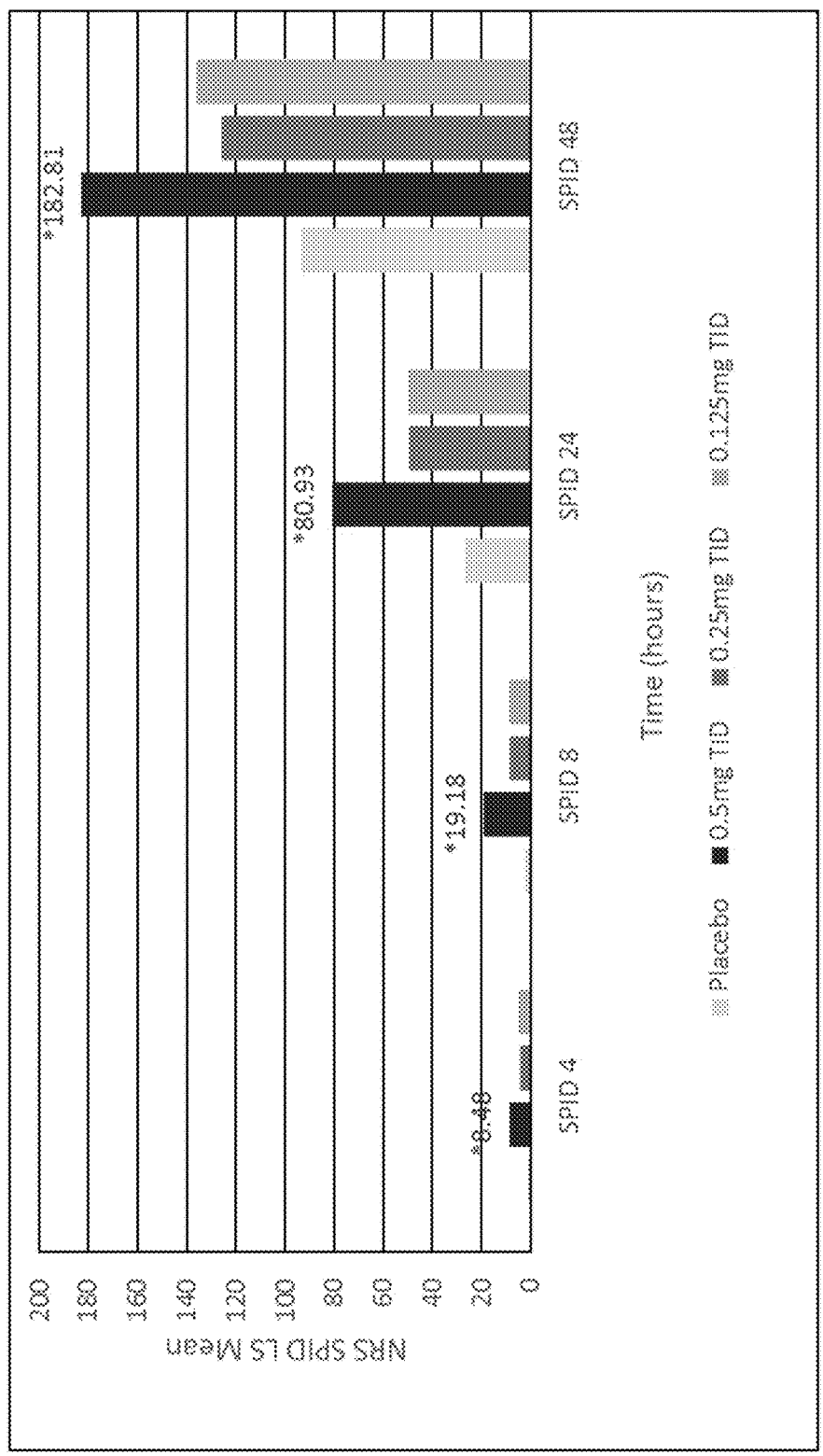
FIG. 2 depicts a chart of a chart of Numeric Rating Scale (NRS) Summed Pain Intensity Difference (SPID) at 4, 8, 24 and 48 hours.

FIG. 2 depicts a chart of Numeric Rating Scale (NRS) Summed Pain Intensity Difference (SPID) at 4, 8, 24 and 48 hours.

Table 45 below describes NRS SPID over 0 to 48 hours (NRS SPID-48) for intention-to-treat (ITT) population.

TABLE 45

Summary of SPID-48
(ITT Population)

| | | Buprenorphine Sublingual Spray | | |
| --- | --- | --- | --- | --- |
| Statistic | Placebo (N = 79) | 0.5 mg TID (N = 81) | 0.25 mg TID (N = 80) | 0.125 mg TID (N = 82) |
| n | 75 | 72 | 75 | 77 |
| mean (SD) | 93.40 (85.063) | 182.81 (107.349) | 125.75 (102.247) | 135.84 (114.040) |
| CV | 91.07 | 58.72 | 81.31 | 83.95 |
| median | 84.0 | 181.0 | 98.0 | 130.3 |
| min, max | −77.7, 377.8 | −17.8, 414.6 | −55.5, 399.0 | −90.5, 399.4 |
| Least square mean(SE)$^a$ | 89.40 (10.109) | 171.33 (10.316) | 125.58 (10.101) | 124.85 (9.944) |
| 95% CI | 69.50, 109.29 | 151.02, 191.63 | 105.70, 145.46 | 105.28, 144.43 |

| Comparison | Least square mean difference (SE)$^a$ | 95% CI | P-value$^a$ |
| --- | --- | --- | --- |
| 0.5 mg vs. placebo | 81.93 (14.283) | 53.82, 110.04 | <0.0001 |
| 0.25 mg vs. placebo | 36.18 (14.099) | 8.43, 63.93 | 0.0108 |
| 0.125 mg vs. placebo | 35.46 (14.020) | 7.86, 63.05 | 0.0120 |

Note:
SPID-48 = Summary of Pain Intensity Differences over 48 hours, CV = coefficient of variation, TID = three times daily.
$^a$Least square means, standard errors(SE), confidence interval(CI) and p-values are from an ANCOVA model with factors for treatment, site and baseline pain intensity.

Table 46 below describes NRS SPID over 0 to 24 hours (NRS SPID-24) for ITT population.

TABLE 46

Summary of SPID-24
(ITT Population)

| | | Buprenorphine Sublingual Spray | | |
| --- | --- | --- | --- | --- |
| Statistic | Placebo (N = 79) | 0.5 mg TID (N = 81) | 0.25 mg TID (N = 80) | 0.125 mg TID (N = 82) |
| n | 75 | 73 | 76 | 77 |
| mean (SD) | 26.61 (42.855) | 80.93 (53.234) | 49.21 (48.223) | 49.90 (56.899) |
| CV | 161.02 | 65.78 | 97.98 | 114.02 |
| median | 21.0 | 83.4 | 43.2 | 48.3 |
| min, max | −46.3, 161.8 | −30.8, 196.9 | −40.9, 177.5 | −62.8, 175.9 |
| Least square mean(SE)$^a$ | 24.16 (5.001) | 75.67 (5.066) | 48.85 (4.962) | 44.17 (4.920) |
| 95% CI | 14.31, 34.00 | 65.70, 85.64 | 39.08, 58.62 | 34.49, 53.86 |

| Comparison | Least square mean difference (SE)$^a$ | 95% CI | P-value$^a$ |
| --- | --- | --- | --- |
| 0.5 mg vs. placebo | 51.51 (7.041) | 37.66, 65.37 | <0.0001 |

TABLE 46-continued

Summary of SPID-24
(ITT Population)

| | | Buprenorphine Sublingual Spray | | |
|---|---|---|---|---|
| Statistic | Placebo (N = 79) | 0.5 mg TID (N = 81) | 0.25 mg TID (N = 80) | 0.125 mg TID (N = 82) |
| 0.25 mg vs. placebo | 24.69 (6.952) | | 11.01, 38.38 | 0.0004 |
| 0.125 mg vs. placebo | 20.02 (6.937) | | 6.37, 33.67 | 0.0042 |

Note:
SPID-24 = Summary of Pain Intensity Differences over 24 hours, CV = coefficient of variation, TID = three times daily.
[a]Least square means, standard errors(SE), confidence interval(CI) and p-values are from an ANCOVA model with factors for treatment, site and baseline pain intensity.

Table 47 below describes NRS SPID over 0 to 8 hours (NRS SPID-8) for ITT population.

TABLE 47

Summary of SPID-8
(ITT Population)

| | | Buprenorphine Sublingual Spray | | |
|---|---|---|---|---|
| Statistic | Placebo (N = 79) | 0.5 mg TID (N = 81) | 0.25 mg TID (N = 80) | 0.125 mg TID (N = 82) |
| n | 77 | 78 | 78 | 78 |
| mean (SD) | 2.14 (13.589) | 19.18 (19.606) | 8.63 (17.661) | 8.71 (18.707) |
| CV | 633.82 | 102.20 | 204.61 | 214.72 |
| median | 0.8 | 19.2 | 7.5 | 6.1 |
| min, max | −25.1, 36.3 | −26.7, 65.3 | −23.3, 63.1 | −27.8, 57.2 |
| Least square mean(SE)[a] | 1.32 (1.851) | 17.57 (1.835) | 8.26 (1.843) | 7.08 (1.837) |
| 95% CI | −2.32, 4.97 | 13.96, 21.18 | 4.63, 11.89 | 3.47, 10.70 |

| Comparison | Least square mean difference (SE)[a] | 95% CI | P-value[a] |
|---|---|---|---|
| 0.5 mg vs. placebo | 16.24 (2.582) | 11.16, 21.32 | <0.0001 |
| 0.25 mg vs. placebo | 6.93 (2.579) | 1.86, 12.01 | 0.0076 |
| 0.125 mg vs. placebo | 5.76 (2.582) | 0.68, 10.84 | 0.0265 |

Note:
SPID-8 = Summary of Pain Intensity Differences over 8 hours, CV = coefficient of variation, TID = three times daily.
[a]Least square means, standard errors(SE), confidence interval(CI) and p-values are from an ANCOVA model with factors for treatment, site and baseline pain intensity.

Table 48 below describes NRS SPID over 0 to 4 hours (NRS SPID-4) for ITT population.

TABLE 48

Summary of SPID-4
(ITT Population)

| | | Buprenorphine Sublingual Spray | | |
|---|---|---|---|---|
| Statistic | Placebo (N = 79) | 0.5 mg TID (N = 81) | 0.25 mg TID (N = 80) | 0.125 mg TID (N = 82) |
| n | 78 | 81 | 80 | 80 |
| mean (SD) | 1.29 (8.466) | 8.48 (10.089) | 4.15 (9.230) | 4.59 (10.637) |
| CV | 656.18 | 119.05 | 222.41 | 231.79 |
| median | 0.0 | 8.2 | 4.0 | 2.9 |
| min, max | −20.3, 25.3 | −19.1, 30.2 | −17.2, 27.1 | −22.2, 28.5 |

TABLE 48-continued

Summary of SPID-4
(ITT Population)

| | | Buprenorphine Sublingual Spray | | |
|---|---|---|---|---|
| Statistic | Placebo (N = 79) | 0.5 mg TID (N = 81) | 0.25 mg TID (N = 80) | 0.125 mg TID (N = 82) |
| Least square mean(SE)[a] | 0.67 (1.036) | 7.70 (1.013) | 3.67 (1.023) | 3.74 (1.020) |
| 95% CI | −1.37, 2.70 | 5.71, 9.69 | 1.66, 5.68 | 1.73, 5.75 |

| Comparison | Least square mean difference (SE)[a] | 95% CI | P-value[a] |
|---|---|---|---|
| 0.5 mg vs. placebo | 7.03 (1.436) | 4.21, 9.86 | <0.0001 |
| 0.25 mg vs. placebo | 3.00 (1.439) | 0.17, 5.84 | 0.0377 |
| 0.125 mg vs. placebo | 3.07 (1.441) | 0.24, 5.91 | 0.0337 |

Note:
SPID-4 = Summary of Pain Intensity Differences over 4 hours, CV = coefficient of variation, TID = three times daily.
[a]Least square means, standard errors(SE), confidence interval(CI) and p-values are from an ANCOVA model with factors for treatment, site and baseline pain intensity.

Table 49 shows time of onset analgesia for investigator initiated trials (IIT) population.

TABLE 49

Time to Onset of Analgesia
(ITT Population)

| | | Buprenorphine Sublingual Spray | | |
|---|---|---|---|---|
| | Placebo (N = 79) | 0.5 mg TID (N = 81) | 0.25 mg TID (N = 80) | 0.125 mg TID (N = 82) |
| Number (%) of subjects with onset of analgesia | 27 (34.2) | 53 (65.4) | 37 (46.3) | 36 (43.9) |
| Number (%) of subjects censored | 52 (65.8) | 28 (34.6) | 43 (53.8) | 46 (56.1) |
| Time (minutes) from first dose to onset of analgesia[a] | | | | |
| 25th percentile (95% CI) | 5.0 (4.0, 83.0) | 6.0 (5.0, 15.0) | 13.0 (5.0, 29.0) | 15.0 (6.0, 27.0) |
| Median (95% CI) | NE | 43.0 (21.0, 64.0) | NE (43.0, NE) | NE (41.0, NE) |
| 75th percentile (95% CI) | NE | NE (101.0, NE) | NE | NE |
| Mean (SE) | 58.4 (4.11) | 146.4 (21.35) | 58.7 (4.46) | 58.3 (4.30) |

| Comparison | P-value[b] |
|---|---|
| 0.5 mg vs. placebo | 0.0010 |
| 0.25 mg vs. placebo | 0.3018 |
| 0.125 mg vs. placebo | 0.3701 |

[a]Percentile estimates and confidence intervals (CI) are from a Kaplan-Meier analysis.
[b]P-value from a log-rank test of each treatment arm vs. placebo
Note:
TID = three times daily, NE = not estimable. Denominator for percentages is the number of subjects per treatment group in the ITT population.
Time to onset of analgesia is the time when the first stopwatch is stopped given that the second stopwatch is stopped.
If the second stopwatch is not stopped, time will be censored at the time of the second dose of study drug or the use of rescue medication, whichever comes first.
If both stopwatches are not stopped, time will be censored at the time of the second dose of study drug or the use of rescue medication whichever comes first.

Figure 3:
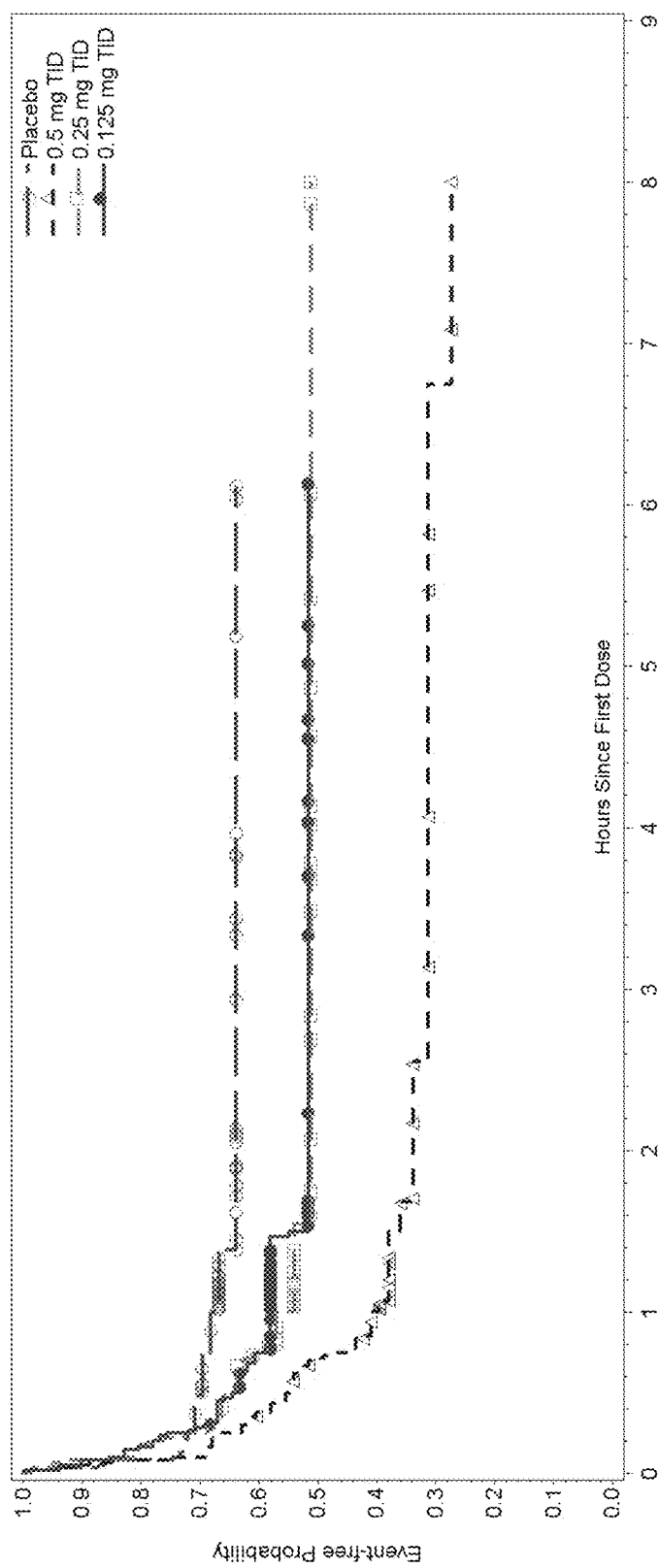
FIG. 3 depicts a chart of time of onset of analgesia for placebo, 0.5 mg tid, 0.25 mg tid and 0.125 tid doses.

FIG. 3 depicts a chart of time of onset of analgesia for placebo, 0.5 mg tid, 0.25 mg tid and 0.125 tid doses.

Table 50 is a representation of mean pain intensity differences by timepoint.

TABLE 50

| Timepoint | Statistic | Placebo (N = 79) | 0.5 mg TID (N = 81) | 0.25 mg TID (N = 80) | 0.125 mg TID (N = 82) |
|---|---|---|---|---|---|
| 5 minutes | n | 79 | 81 | 80 | 82 |
| | mean (SD) | 0.3 (1.06) | 0.5 (1.15) | 0.3 (1.01) | 0.3 (0.75) |
| 15 minutes | n | 79 | 81 | 80 | 82 |
| | mean (SD) | 0.6 (1.76) | 0.4 (1.39) | 0.6 (1.56) | 0.6 (1.55) |
| 30 minutes | n | 79 | 81 | 80 | 82 |
| | mean (SD) | 0.7 (2.15) | 0.6 (1.65) | 0.7 (2.12) | 0.7 (2.18) |
| 45 minutes | n | 79 | 81 | 80 | 81 |
| | mean (SD) | 0.6 (2.38) | 1.1 (2.08) | 0.9 (2.13) | 1.0 (2.41) |
| 1 hour | n | 79 | 81 | 80 | 81 |
| | mean (SD) | 0.6 (2.58) | 1.5 (2.40) | 1.0 (2.37) | 1.1 (2.62) |
| 1.5 hours | n | 78 | 81 | 80 | 80 |
| | mean (SD) | 0.6 (2.77) | 2.1 (2.72) | 1.2 (2.58) | 1.2 (2.91) |
| 2 hours | n | 78 | 81 | 79 | 80 |
| | mean (SD) | 0.5 (2.77) | 2.4 (3.07) | 1.2 (2.62) | 1.3 (3.05) |
| 3 hours | n | 78 | 81 | 80 | 80 |
| | mean (SD) | 0.2 (2.35) | 2.7 (3.09) | 1.3 (2.95) | 1.3 (3.22) |
| 4 hours | n | 78 | 81 | 80 | 80 |
| | mean (SD) | −0.1 (2.13) | 2.6 (3.26) | 0.9 (3.14) | 1.1 (3.21) |
| 5 hours | n | 77 | 80 | 79 | 80 |
| | mean (SD) | −0.4 (2.08) | 2.6 (3.06) | 0.8 (3.14) | 1.2 (3.32) |
| 6 hours | n | 78 | 78 | 79 | 79 |
| | mean (SD) | 0.2 (2.16) | 3.1 (3.16) | 1.1 (3.16) | 1.1 (3.19) |
| 7 hours | n | 77 | 79 | 79 | 78 |
| | mean (SD) | 0.4 (2.11) | 3.0 (3.06) | 1.3 (2.88) | 0.9 (2.93) |
| 8 hours | n | 77 | 78 | 78 | 78 |
| | mean (SD) | 0.5 (2.10) | 2.5 (3.06) | 1.2 (2.78) | 0.7 (2.73) |
| 12 hours | n | 75 | 78 | 77 | 78 |
| | mean (SD) | 1.0 (2.50) | 3.7 (2.78) | 2.2 (2.88) | 2.0 (3.40) |
| 16 hours | n | 75 | 76 | 76 | 77 |
| | mean (SD) | 0.9 (2.11) | 3.4 (2.65) | 1.9 (2.63) | 1.9 (3.16) |
| 20 hours | n | 75 | 75 | 76 | 77 |
| | mean (SD) | 2.1 (2.90) | 4.3 (2.70) | 3.2 (2.69) | 3.1 (3.07) |
| 24 hours | n | 75 | 73 | 76 | 77 |
| | mean (SD) | 2.2 (2.59) | 4.0 (2.64) | 3.0 (2.72) | 3.2 (2.98) |
| 32 hours | n | 75 | 72 | 75 | 77 |
| | mean (SD) | 2.4 (2.48) | 3.9 (2.89) | 2.9 (2.80) | 3.4 (2.90) |
| 40 hours | n | 75 | 71 | 75 | 77 |
| | mean (SD) | 2.5 (2.21) | 3.9 (2.81) | 3.2 (2.58) | 3.3 (2.80) |
| 48 hours | n | 75 | 72 | 75 | 77 |
| | mean (SD) | 3.5 (2.60) | 4.9 (2.33) | 3.5 (3.00) | 4.1 (2.89) |

The conclusions are as follows:

Primary Efficacy

The largest pain reduction (NRS SPID-48) was observed for the 0.5 mg TID BSS group.

Statistically significantly larger reductions in NRS SPID-48 compared to placebo for the 0.5 mg TID BSS p-value: <0.0001. The largest reduction in NRS SPID-48 compared to placebo was observed for the 0.5 mg TID BSS treatment group.

Secondary Efficacy

Largest pain reductions (NRS SPID-4, NRS SPID-8, and NRS SPID-24) were observed for 0.5 mg TID BSS group (p-value: <0.0001). Secondary time points at 4, 8 and 24 hours SPID were all statistically significantly different.

Example 9: Pharmacokinetic Data for Formulation 20

Objective

The primary objective of this study was to compare the bioavailability of a test formulation of Buprenorphine-Naloxone Sublingual (SL) spray, 6.5 mg/1.63 mg (1 spray) to that of a single dose of Suboxone® (buprenorphine and naloxone) sublingual film, 12 mg/3 mg, under fasted conditions. The secondary objective was to evaluate the safety and tolerability of Buprenorphine-Naloxone SL spray.

Study Design

This was a single-dose, open-label, randomized, two-period, two-treatment crossover study. Fifty-six healthy subjects were enrolled. Subjects who successfully completed the screening process checked into the research center the evening before first dose. Subjects who continued to meet inclusion/exclusion criteria the morning of dose were assigned a subject number, based on the order in which they successfully completed the screening process and procedures as outlined in the study protocol. Subjects were randomly assigned to a treatment sequence and received two separate single-dose administrations of study medication, one treatment per period, according to the randomization schedule. Dosing days were separated by a washout period of at least 14 days.

Subjects received each of the treatments listed below during the two treatment periods:

Treatment A: Test Product

Buprenorphine Naloxone SL spray, 6.5 mg/1.63 mg

Dose=1 sublingual spray (total dose 6.5 mg/1.63 mg)

Treatment B: Reference Product

Suboxone® (buprenorphine and naloxone) sublingual film, 12 mg/3 mg

Dose=1×12 mg/3 mg sublingual film

Clinical Procedures Summary

During each study period, 6 mL blood samples were obtained for buprenorphine, norbuprenorphine, and unconjugated naloxone analysis before and after each dose at selected times through 144 hours after dose administration. A total of 34 pharmacokinetic (PK) blood samples were collected from each subject for buprenorphine, norbuprenorphine, and unconjugated naloxone, 17 samples in each study period. In addition, 6 mL blood samples were obtained for total naloxone analysis before and after each dose at selected times through 72 hours after dose administration. A total of 28 PK blood samples were collected from each subject for naloxone analysis, 14 samples in each study period.

Procedures for Collecting Samples for Pharmacokinetic Analysis

Blood samples (1×6 mL) for buprenorphine, norbuprenorphine, and unconjugated naloxone analysis were collected at 0 (predose), and at 5 minutes, 10 minutes, 15 minutes, 30 minutes, and 1, 2, 4, 8, 12, 24, 36, 48, 72, 96, 120, and 144 hours.

Blood samples (1×6 mL) for total naloxone analysis were collected at 0 (predose), and at 5 minutes, 10 minutes, 15 minutes, 30 minutes, and 1, 2, 4, 8, 12, 24, 36, 48, and 72 hours.

Bioanalytical Summary

Plasma samples were analyzed for buprenorphine, norbuprenorphine, unconjugated naloxone, and total naloxone by Worldwide Clinical Trials (WCT) using validated LC-MS-MS procedures. The methods were validated for ranges of 20.0 to 10,000 pg/mL for buprenorphine and norbuprenorphine and 2.00 to 1000 pg/mL for unconjugated naloxone, based on the analysis of 1.00 mL of human EDTA plasma, and 0.0500 to 50.0 ng/mL for total naloxone, based on the analysis of 0.200 mL of human EDTA plasma. Data were stored in Watson Laboratory Information Management System (LIMS; Version 7.2.0.03, Thermo Fisher Scientific).

Pharmacokinetic Analysis

Concentration-time data were analyzed using noncompartmental methods in Phoenix™ WinNonlin® (Version 6.3, Pharsight Corporation). Concentration-time data that were below the limit of quantification (BLQ) were treated as zero in the data summarization and descriptive statistics. In the pharmacokinetic analysis, BLQ concentrations were treated as zero from time-zero up to the time at which the first quantifiable concentration was observed; embedded and/or terminal BLQ concentrations were treated as "missing". Actual sample times were used in the pharmacokinetic analysis. The linear trapezoidal method was used to calculation the area under the curve (AUC).

The following pharmacokinetic parameters were calculated: peak concentration in plasma ($C_{max}$), time to peak concentration ($T_{max}$), elimination rate constant ($\lambda_z$), terminal half-life ($T_{1/2}$), area under the concentration-time curve from time-zero to the time of the last quantifiable concentration ($AUC_{last}$), area under the plasma concentration time curve from time-zero extrapolated to infinity ($AUC_{inf}$), the percent of $AUC_{inf}$ based on extrapolation ($AUC_{extrap}$), last quantifiable plasma concentration ($C_{last}$), and time of the last quantifiable plasma concentration ($T_{last}$). In addition, partial AUCs $AUC_{0-72}$, $AUC_{0-96}$, $AUC_{0-120}$, and $AUC_{0-144}$ were estimated for buprenorphine and unconjugated naloxone to provide information regarding systemic exposure at different times during the extended pharmacokinetic sampling interval.

Analysis of variance (ANOVA) and the Schuirmann's two one-sided t-test procedure at the 5% significance level were applied to the log-transformed pharmacokinetic exposure parameters, $C_{max}$, $AUC_{last}$, and $AUC_{inf}$ for buprenorphine, norbuprenorphine, unconjugated naloxone, and total naloxone. The ratio of the geometric means (Insys Sublingual Spray-Test/Suboxone Sublingual Film-Reference) was reported along with the 90% confidence interval about the ratio. For informational purposes, $AUC_{0-72}$, $AUC_{0-96}$, $AUC_{0-120}$, and $AUC_{0-144}$ for buprenorphine and unconjugated naloxone were compared across treatments using an analogous statistical method.

Results and Discussion

Data from 50 subjects who completed at least one study period were included in the pharmacokinetic and statistical analyses. Mean concentration-time data are shown in Tables 51 through 54. Results of the pharmacokinetic and statistical analyses are shown below in Tables 55 through 64.

Buprenorphine

Overall, the pharmacokinetic profile of buprenorphine after the administration of Buprenorphine Naloxone SL spray, 6.5 mg/1.63 mg was similar to that after the administration of Suboxone Sublingual Film 12 mg/3 mg. From the mean buprenorphine concentration-time profiles, the concentrations achieved after the Sublingual Spray were comparable to those after Suboxone, even though a much lower Sublingual Spray dose was administered (6.5 mg in Sublingual Spray vs. 12 mg in Suboxone). At early time points and through approximately 24 hours, the mean buprenorphine concentration-time profiles were practically superimposable for the two treatments; at latter time points, minor differences were noted, with the mean buprenorphine concentrations after the Sublingual Spray being slightly lower than those after Suboxone. These trends were reflected in the derived pharmacokinetic parameters. No appreciable differences were noted in the mean buprenorphine $C_{max}$ across treatments (5670±1590 pg/mL after Sublingual Spray, 6210±3110 pg/mL after Suboxone). No appreciable differences were noted in the mean±SD buprenorphine $AUC_{0-72}$, $AUC_{0-96}$, $AUC_{0-144}$, $AUC_{last}$, and $AUC_{inf}$. For example, mean $AUC_{last}$ was 46660±12980 h*pg/mL after Sublingual Spray and 56100±21460 h*pg/mL after Suboxone. Due to the extended pharmacokinetic sampling interval used in this study, AUC to the last quantifiable sample ($AUC_{last}$) provided a reasonable estimate of the overall systemic exposure ($AUC_{inf}$ extrapolated to infinity). Mean $AUC_{inf}$ values were 48790±13810 h*pg/mL after Sublingual Spray and 59240±22500 h*pg/mL after Suboxone. On average, only 4.27 to 5.28% of $AUC_{inf}$ was based on extrapolation.

It should be noted that some degree of pharmacokinetic variability was observed, in particular for Suboxone relative to that for the Sublingual Spray; the intersubject variability (CV %) for $C_{max}$ and AUCs ranged from 27.81 to 28.31% for the Sublingual Spray and 37.98 to 50.02% for Suboxone. It was also noted that a differential location shift existed between the mean and median AUC values for Suboxone; the mean $AUC_{last}$ and $AUC_{inf}$ values for Suboxone were higher than the median, suggesting that the data were skewed toward the upper range. The differential distribution of the $AUC_{inf}$ values between the two treatments may have contributed to the ANOVA results for this metric (discussed below).

From the statistical analysis log-transformed pharmacokinetic parameters using an ANOVA model, the geometric mean ratios (90% confidence interval) for buprenorphine $C_{max}$, $AUC_{last}$, and $AUC_{inf}$ were 96.01% (88.29, 104.42%), 86.11% (80.44, 92.18%), and 85.19% (79.64, 91.12%), respectively. The ANOVA results for buprenorphine $AUC_{0-72}$, $AUC_{0-96}$, $AUC_{0-120}$, and $AUC_{0-144}$ were 88.40% (82.59, 94.62%), 87.37% (81.68, 93.46%), 86.75% (81.12, 92.77%), and 86.31% (80.72, 92.29%), respectively. Hence, based on actual data over the 144-hour sampling interval (and over truncated intervals through 72, 96, 120 and 144 hours), bioequivalence criteria were met for buprenorphine in comparisons of the Sublingual Spray to Suboxone. The lower 90% confidence interval for the extrapolated AUC ($AUC_{inf}$) was 79.64%, 0.36% below the standard bioequivalence limit (80.00%) using the two one-sided tests procedure.

Norbuprenorphine

Exposure to norbuprenorphine differed across treatments. Based on mean estimates of $C_{max}$ and AUCs, exposure to norbuprenorphine was 2- to 2.6-fold lower after the Sublingual Spray relative to Suboxone, possibly due to increased direct absorption into systemic circulation and lower presystemic, first-pass metabolism for the Sublingual Spray.

Unconjugated Naloxone

Overall, the pharmacokinetic profile of unconjugated naloxone after the administration of Buprenorphine Naloxone SL spray, 6.5 mg/1.63 mg was similar to that after the administration of Suboxone Sublingual Film 12 mg/3 mg. Based on mean estimates of $C_{max}$ and AUCs, exposure to unconjugated naloxone was comparable across treatments. Mean $C_{max}$ was 379±211 pg/mL after Sublingual Spray and 356±149 pg/mL after Suboxone; mean $AUC_{last}$ was 887.6±445.4 h*pg/mL after Sublingual Spray and 942.0±430.1 h*pg/mL after Suboxone. $AUC_{inf}$ were similar to $AUC_{last}$ values; due to the relatively short $T_{1/2}$ of unconjugated naloxone (approximately 3 to 4 hours), only 2.18 to 2.41% of $AUC_{inf}$ was based on extrapolation.

From the statistical analysis log-transformed pharmacokinetic parameters using an ANOVA model, the geometric mean ratios (90% confidence interval) for unconjugated naloxone $C_{max}$, $AUC_{last}$, and $AUC_{inf}$ were 103.72% (93.78, 114.71%), 94.95% (86.93, 103.72%), and 94.69% (86.79, 103.31%), respectively. The ANOVA results for unconjugated naloxone $AUC_{0-72}$, $AUC_{0-96}$, $AUC_{0-120}$, and $AUC_{0-144}$ were comparable to those for $AUC_{last}$ and $AUC_{inf}$. Hence, bioequivalence criteria were met for all pharmacokinetic metrics considered in the analysis.

Total Naloxone

Exposure to total naloxone differed across treatments. Based on mean estimates of $C_{max}$ and AUCs, exposure to total naloxone was approximately 2-fold lower after the Sublingual Spray relative to Suboxone, possibly due to increased direct absorption into systemic circulation and lower presystemic, first-pass metabolism/glucuronidation for the Sublingual Spray.

Conclusions

Overall, the pharmacokinetic profile of buprenorphine after the administration of Buprenorphine Naloxone SL spray, 6.5 mg/1.63 mg was similar to that after the administration of Suboxone Sublingual Film 12 mg/3 mg. No significant differences in $C_{max}$ and AUCs over the 144-hour pharmacokinetic sampling period were observed and bioequivalence criteria (90% confidence intervals within 80.00-125.00%) were met for the AUC at 72 hours (82.6%-94.6%), 96 hours (81.7%-93.5%), 120 hours (81.1%-92.8%), and 144 hours (80.7%-92.3%) postdose. The lower 90% confidence interval for the extrapolated AUC ($AUC_{inf}$) was 79.64%, 0.36% below the bioequivalence limit of 80.00%. Therefore, based on data acquired over an extended sampling period (144 hours or 6 days), Buprenorphine Naloxone SL spray, 6.5 mg/1.63 mg is considered essentially bioequivalent to Sublingual Film 12 mg/3 mg.

The pharmacokinetic profile of unconjugated naloxone after the administration of Buprenorphine Naloxone SL spray, 6.5 mg/1.63 mg was similar to that after the administration of Suboxone Sublingual Film 12 mg/3 mg. No significant differences in $C_{max}$ and AUCs were observed and bioequivalence criteria (90% confidence intervals within 80.00-125.00%) were met for all pharmacokinetic metrics considered in the analysis.

TABLE 51

Buprenorphine Concentration-Time Data after Administration of the Test Product (Treatment A) and the Reference Product (Treatment B).

| Time (h) | Treatment A: Test Product | | | | Treatment B: Reference Product (Suboxone) | | | |
|---|---|---|---|---|---|---|---|---|
| | n | Mean (pg/mL) | SD (pg/mL) | CV (%) | n | Mean (pg/mL) | SD (pg/mL) | CV (%) |
| 0.00 | 50 | 0.00 | 0.00 | NC | 49 | 0.00 | 0.00 | NC |
| 0.08 | 49 | 36.9 | 66.2 | 179.77 | 49 | 1.30 | 9.13 | 700.00 |
| 0.17 | 50 | 491 | 463 | 94.30 | 49 | 50.2 | 73.9 | 147.10 |
| 0.25 | 50 | 1220 | 902 | 74.02 | 49 | 254 | 255 | 100.57 |
| 0.50 | 50 | 3270 | 1570 | 48.13 | 49 | 2300 | 1690 | 73.45 |
| 1.00 | 50 | 4990 | 1690 | 33.93 | 49 | 5130 | 3060 | 59.61 |
| 2.00 | 50 | 5420 | 1530 | 28.14 | 49 | 5440 | 2300 | 42.27 |
| 4.00 | 50 | 3580 | 1270 | 35.49 | 49 | 3660 | 2080 | 56.97 |
| 8.00 | 50 | 1150 | 407 | 35.36 | 49 | 1360 | 983 | 72.21 |
| 12.00 | 50 | 576 | 181 | 31.50 | 49 | 798 | 423 | 53.06 |
| 24.00 | 50 | 293 | 90.6 | 30.94 | 49 | 448 | 166 | 37.07 |
| 36.00 | 50 | 212 | 73.7 | 34.76 | 49 | 329 | 121 | 36.70 |
| 48.00 | 50 | 144 | 53.2 | 36.84 | 49 | 218 | 86.4 | 39.56 |
| 72.00 | 50 | 88.8 | 37.2 | 41.95 | 49 | 133 | 54.2 | 40.70 |
| 96.00 | 50 | 59.9 | 28.1 | 46.83 | 49 | 87.6 | 40.6 | 46.40 |
| 120.00 | 50 | 37.6 | 25.0 | 66.57 | 49 | 59.2 | 31.1 | 52.45 |
| 144.00 | 50 | 25.5 | 21.7 | 85.24 | 48 | 42.1 | 30.9 | 73.38 |

Note:
Plasma samples analyzed using a bioanalytical method with a validated range 20.0 to 10,000 pg/mL; concentrations reported in pg/mL to 3 significant figures; concentrations below limit of quantification set to zero (0.00 pg/mL) in the data summarization
NC = Not calculated

TABLE 52

Norbuprenorphine Concentration-Time Data after Administration of the Test Product (Treatment A) and the Reference Product (Treatment B).

| | Treatment A: Test Product | | | | Treatment B: Reference Product (Suboxone) | | | |
|---|---|---|---|---|---|---|---|---|
| Time (h) | n | Mean (pg/mL) | SD (pg/mL) | CV (%) | n | Mean (pg/mL) | SD (pg/mL) | CV (%) |
| 0.00 | 50 | 0.418 | 2.96 | 707.11 | 49 | 0.567 | 3.97 | 700.00 |
| 0.08 | 49 | 1.04 | 5.09 | 489.80 | 49 | 0.651 | 4.56 | 700.00 |
| 0.17 | 50 | 30.4 | 60.1 | 197.69 | 49 | 3.59 | 12.7 | 353.54 |
| 0.25 | 50 | 137 | 203 | 147.89 | 49 | 41.1 | 89.5 | 217.66 |
| 0.50 | 50 | 456 | 421 | 92.37 | 49 | 800 | 1000 | 125.44 |
| 1.00 | 50 | 684 | 478 | 69.85 | 49 | 1990 | 1650 | 82.59 |
| 2.00 | 50 | 740 | 415 | 56.01 | 49 | 1800 | 1080 | 60.10 |
| 4.00 | 50 | 614 | 304 | 49.60 | 49 | 1260 | 674 | 53.60 |
| 8.00 | 50 | 522 | 235 | 45.03 | 49 | 1020 | 535 | 52.18 |
| 12.00 | 50 | 470 | 217 | 46.21 | 49 | 945 | 469 | 49.62 |
| 24.00 | 50 | 466 | 199 | 42.64 | 49 | 984 | 482 | 49.04 |
| 36.00 | 50 | 390 | 150 | 38.38 | 49 | 828 | 384 | 46.44 |
| 48.00 | 50 | 304 | 132 | 43.32 | 49 | 633 | 302 | 47.76 |
| 72.00 | 50 | 212 | 107 | 50.44 | 49 | 435 | 234 | 53.80 |
| 96.00 | 50 | 151 | 87.5 | 57.93 | 49 | 302 | 172 | 56.88 |
| 120.00 | 50 | 108 | 74.4 | 68.68 | 49 | 213 | 141 | 65.91 |
| 144.00 | 50 | 86.3 | 67.1 | 77.79 | 48 | 171 | 132 | 77.70 |

Note:
Plasma samples analyzed using a bioanalytical method with a validated range 20.0 to 10,000 pg/mL; concentrations reported in pg/mL to 3 significant figures; concentrations below limit of quantification set to zero (0.00 pg/mL) in the data summarization

TABLE 53

Unconjugated Naloxone Concentration-Time Data after Administration of the Test Product (Treatment A) and the Reference Product (Treatment B).

| | Treatment A: Test Product | | | | Treatment B: Reference Product (Suboxone) | | | |
|---|---|---|---|---|---|---|---|---|
| Time (h) | n | Mean (pg/mL) | SD (pg/mL) | CV (%) | n | Mean (pg/mL) | SD (pg/mL) | CV (%) |
| 0.00 | 50 | 0.00 | 0.00 | NC | 49 | 0.00 | 0.00 | NC |
| 0.08 | 49 | 50.4 | 51.9 | 103.09 | 49 | 5.08 | 17.7 | 349.10 |
| 0.17 | 50 | 205 | 171 | 83.54 | 49 | 47.5 | 75.0 | 157.82 |
| 0.25 | 50 | 292 | 232 | 79.37 | 49 | 105 | 99.0 | 94.56 |
| 0.50 | 50 | 349 | 199 | 57.08 | 49 | 294 | 164 | 55.74 |
| 1.00 | 50 | 293 | 140 | 47.98 | 49 | 304 | 120 | 39.42 |
| 2.00 | 50 | 166 | 84.8 | 50.93 | 49 | 177 | 86.5 | 48.78 |
| 4.00 | 50 | 54.3 | 30.3 | 55.76 | 49 | 66.8 | 64.8 | 96.90 |
| 8.00 | 50 | 9.06 | 4.90 | 54.14 | 49 | 14.3 | 15.7 | 109.92 |
| 12.00 | 50 | 3.67 | 3.56 | 97.16 | 49 | 6.80 | 6.47 | 95.25 |
| 24.00 | 50 | 0.705 | 1.87 | 265.19 | 49 | 2.14 | 3.18 | 148.44 |
| 36.00 | 50 | 0.00 | 0.00 | NC | 49 | 0.219 | 0.749 | 341.25 |
| 48.00 | 50 | 0.00 | 0.00 | NC | 49 | 0.00 | 0.00 | NC |
| 72.00 | 50 | 0.00 | 0.00 | NC | 49 | 0.00 | 0.00 | NC |
| 96.00 | 50 | 0.00 | 0.00 | NC | 49 | 0.00 | 0.00 | NC |
| 120.00 | 49 | 0.00 | 0.00 | NC | 49 | 0.00 | 0.00 | NC |
| 144.00 | 50 | 0.00 | 0.00 | NC | 48 | 0.00 | 0.00 | NC |

Note:
Plasma samples analyzed using a bioanalytical method with a validated range 2.00 to 1000 pg/mL; concentrations reported in pg/mL to 3 significant figures; concentrations below limit of quantification set to zero (0.00 pg/mL) in the data summarization
NC = Not calculated

TABLE 54

Total Naloxone Concentration-Time Data after Administration of the Test Product (Treatment A) and the Reference Product (Treatment B).

| | Treatment A: Test Product | | | | Treatment B: Reference Product (Suboxone) | | | |
|---|---|---|---|---|---|---|---|---|
| Time (h) | n | Mean (ng/mL) | SD (ng/mL) | CV (%) | n | Mean (ng/mL) | SD (ng/mL) | CV (%) |
| 0.00 | 50 | 0.00 | 0.00 | NC | 49 | 0.00 | 0.00 | NC |
| 0.08 | 49 | 0.150 | 0.275 | 183.48 | 49 | 0.0285 | 0.0991 | 347.54 |

TABLE 54-continued

Total Naloxone Concentration-Time Data after Administration of the
Test Product (Treatment A) and the Reference Product (Treatment B).

| Time (h) | Treatment A: Test Product | | | | Treatment B: Reference Product (Suboxone) | | | |
|---|---|---|---|---|---|---|---|---|
| | n | Mean (ng/mL) | SD (ng/mL) | CV (%) | n | Mean (ng/mL) | SD (ng/mL) | CV (%) |
| 0.17 | 50 | 1.44 | 1.81 | 125.87 | 49 | 0.416 | 0.976 | 234.70 |
| 0.25 | 50 | 4.14 | 4.12 | 99.53 | 49 | 2.50 | 4.94 | 197.40 |
| 0.50 | 50 | 8.90 | 6.50 | 73.10 | 49 | 15.7 | 14.1 | 89.82 |
| 1.00 | 50 | 9.19 | 4.45 | 48.44 | 49 | 21.3 | 10.2 | 48.03 |
| 2.00 | 50 | 5.02 | 2.75 | 54.78 | 49 | 9.76 | 4.53 | 46.43 |
| 4.00 | 50 | 1.50 | 0.960 | 64.13 | 49 | 2.67 | 1.33 | 49.92 |
| 8.00 | 50 | 0.846 | 0.554 | 65.50 | 49 | 1.42 | 1.10 | 77.40 |
| 12.00 | 50 | 0.626 | 0.688 | 109.87 | 49 | 1.05 | 0.514 | 48.83 |
| 24.00 | 50 | 0.211 | 0.121 | 57.26 | 49 | 0.428 | 0.281 | 65.62 |
| 36.00 | 50 | 0.0583 | 0.0680 | 116.78 | 49 | 0.126 | 0.0975 | 77.13 |
| 48.00 | 50 | 0.0101 | 0.0281 | 278.20 | 49 | 0.0520 | 0.0733 | 141.05 |
| 72.00 | 50 | 0.00110 | 0.00778 | 707.11 | 49 | 0.00263 | 0.0129 | 490.72 |

Note:
Plasma samples analyzed using a bioanalytical method with a validated range 0.0500 to 50.0 ng/mL; concentrations reported in ng/mL to 3 significant figures; concentrations below limit of quantification set to zero (0.00 ng/mL) in the data summarization
NC = Not calculated

TABLE 55

Pharmacokinetic Parameters of Buprenorphine.

| Parameter | Treatment A: Test Product | | | | Treatment B: Reference Product (Suboxone) | | | |
|---|---|---|---|---|---|---|---|---|
| | n | Mean | SD | CV % | n | Mean | SD | CV % |
| $T_{max}$ (h) | 50 | 1.63 | 0.50 | 30.77 | 49 | 1.66 | 0.72 | 43.56 |
| Median (Range) | | 2.00 | (0.50-2.00) | | | 2.00 | (0.50-4.00) | |
| $C_{max}$ (pg/mL) | 50 | 5670 | 1590 | 28.08 | 49 | 6210 | 3110 | 50.02 |
| $AUC_{last}$ (h*pg/mL) | 50 | 46660 | 12980 | 27.81 | 49 | 56100 | 21460 | 38.25 |
| $AUC_{inf}$ (h*pg/mL) | 50 | 48790 | 13810 | 28.31 | 49 | 59240 | 22500 | 37.98 |
| $AUC_{0-72}$ (h*pg/mL) | 50 | 43040 | 11670 | 27.11 | 49 | 50560 | 19670 | 38.91 |
| $AUC_{0-96}$ (h*pg/mL) | 50 | 44830 | 12140 | 27.07 | 49 | 53210 | 20390 | 38.32 |
| $AUC_{0-120}$ (h*pg/mL) | 50 | 46030 | 12500 | 27.16 | 49 | 54980 | 20910 | 38.04 |
| $AUC_{0-144}$ (h*pg/mL) | 50 | 46860 | 12790 | 27.30 | 49 | 56230 | 21320 | 37.92 |
| $AUC_{Extrap}$ (%) | 50 | 4.27 | 2.13 | 49.83 | 49 | 5.28 | 3.01 | 57.02 |
| $\lambda_z$ (h$^{-1}$) | 50 | 0.0175 | 0.0043 | 24.51 | 49 | 0.0172 | 0.0041 | 23.74 |
| $T_{1/2}$ (h) | 50 | 41.84 | 10.15 | 24.26 | 49 | 42.72 | 10.38 | 24.30 |
| $T_{last}$ (h) | 50 | 133.44 | 18.24 | 13.67 | 49 | 137.60 | 14.50 | 10.54 |
| $C_{last}$ (pg/mL) | 50 | 33.2 | 15.3 | 46.10 | 49 | 47.2 | 24.8 | 52.46 |

TABLE 56

Pharmacokinetic Parameters of Norbuprenorphine

| Parameter | Treatment A: Test Product | | | | Treatment B: Reference Product (Suboxone) | | | |
|---|---|---|---|---|---|---|---|---|
| | n | Mean | SD | CV % | n | Mean | SD | CV % |
| $T_{max}$ (h) | 50 | 3.49 | 5.54 | 158.73 | 49 | 3.98 | 7.39 | 185.67 |
| Median (Range) | | 2.00 | (0.50-24.00) | | | 1.00 | (0.50-36.00) | |
| $C_{max}$ (pg/mL) | 50 | 854 | 461 | 53.99 | 49 | 2220 | 1540 | 69.12 |
| $AUC_{last}$ (h*pg/mL) | 50 | 37570 | 14560 | 38.75 | 49 | 77800 | 34820 | 44.76 |
| $AUC_{inf}$ (h*pg/mL) | 50 | 46870 | 22370 | 47.72 | 49 | 93460 | 47480 | 50.81 |
| $AUC_{Extrap}$ (%) | 50 | 16.39 | 13.43 | 81.94 | 49 | 14.15 | 10.41 | 73.53 |
| $\lambda_z$ (h$^{-1}$) | 50 | 0.0159 | 0.0076 | 47.52 | 49 | 0.0159 | 0.0060 | 37.45 |
| $T_{1/2}$ (h) | 50 | 56.50 | 34.49 | 61.05 | 49 | 50.97 | 23.27 | 45.66 |
| $T_{last}$ (h) | 50 | 141.12 | 9.25 | 6.56 | 49 | 143.48 | 3.42 | 2.39 |
| $C_{last}$ (pg/mL) | 50 | 89.3 | 63.8 | 71.43 | 49 | 173 | 132 | 76.44 |

TABLE 57

Pharmacokinetic Parameters of Unconjugated Naloxone

| Parameter | Treatment A: Test Product | | | | Treatment B: Reference Product (Suboxone) | | | |
|---|---|---|---|---|---|---|---|---|
| | n | Mean | SD | CV % | n | Mean | SD | CV % |
| $T_{max}$ (h) | 50 | 0.56 | 0.28 | 50.10 | 49 | 0.84 | 0.56 | 66.81 |
| Median (Range) | | 0.50 | (0.17-1.03) | | | 1.00 | (0.25-4.00) | |
| $C_{max}$ (pg/mL) | 50 | 379 | 211 | 55.76 | 49 | 356 | 149 | 41.75 |
| $AUC_{last}$ (h*pg/mL) | 50 | 887.6 | 445.4 | 50.18 | 49 | 942.0 | 430.1 | 45.66 |
| $AUC_{inf}$ (h*pg/mL) | 50 | 904.9 | 445.9 | 49.27 | 48 | 942.0 | 411.0 | 43.63 |
| $AUC_{0-72}$ (h*pg/mL) | 50 | 903.4 | 446.3 | 49.40 | 48 | 941.1 | 410.6 | 43.63 |
| $AUC_{0-96}$ (h*pg/mL) | 50 | 904.0 | 446.1 | 49.35 | 48 | 941.6 | 410.9 | 43.64 |
| $AUC_{0-120}$ (h*pg/mL) | 50 | 904.3 | 446.0 | 49.32 | 48 | 941.7 | 411.0 | 43.64 |
| $AUC_{0-144}$ (h*pg/mL) | 50 | 904.5 | 445.9 | 49.30 | 48 | 941.8 | 411.0 | 43.64 |
| $AUC_{Extrap}$ (%) | 50 | 2.18 | 2.79 | 128.30 | 48 | 2.41 | 1.33 | 55.07 |
| $\lambda_z$ (h$^{-1}$) | 50 | 0.3617 | 0.1584 | 43.79 | 48 | 0.2547 | 0.1450 | 56.93 |
| $T_{1/2}$ (h) | 50 | 3.48 | 5.51 | 158.21 | 48 | 4.15 | 3.07 | 74.06 |
| $T_{last}$ (h) | 50 | 13.44 | 5.58 | 41.55 | 49 | 18.37 | 8.28 | 45.10 |
| $C_{last}$ (pg/mL) | 50 | 4.00 | 1.90 | 47.39 | 49 | 4.51 | 3.29 | 72.93 |

TABLE 58

Pharmacokinetic Parameters of Total Naloxone

| Parameter | Treatment A: Test Product | | | | Treatment B: Reference Product (Suboxone) | | | |
|---|---|---|---|---|---|---|---|---|
| | n | Mean | SD | CV % | n | Mean | SD | CV % |
| $T_{max}$ (h) | 50 | 1.40 | 2.13 | 152.59 | 49 | 1.12 | 1.14 | 101.89 |
| Median (Range) | | 1.00 | (0.25-12.00) | | | 1.00 | (0.50-8.00) | |
| $C_{max}$ (ng/mL) | 50 | 12.0 | 5.38 | 44.86 | 49 | 24.9 | 11.9 | 47.75 |
| $AUC_{last}$ (h*ng/mL) | 50 | 34.12 | 10.51 | 30.80 | 49 | 65.80 | 20.43 | 31.04 |
| $AUC_{inf}$ (h*ng/mL) | 48 | 36.22 | 10.45 | 28.84 | 49 | 66.99 | 20.39 | 30.44 |
| $AUC_{Extrap}$ (%) | 48 | 4.48 | 2.92 | 65.21 | 49 | 2.31 | 2.89 | 124.97 |
| $\lambda_z$ (h$^{-1}$) | 48 | 0.0911 | 0.0377 | 41.37 | 49 | 0.0923 | 0.0277 | 30.03 |
| $T_{1/2}$ (h) | 48 | 8.71 | 3.31 | 38.00 | 49 | 8.24 | 2.71 | 32.85 |
| $T_{last}$ (h) | 50 | 32.16 | 10.41 | 32.37 | 49 | 41.14 | 10.95 | 26.63 |
| $C_{last}$ (ng/mL)ANO | 50 | 0.122 | 0.0587 | 48.20 | 49 | 0.0987 | 0.0575 | 58.20 |

TABLE 59

Statistical Analysis of the Log-Transformed Systemic Exposure Parameters of Buprenorphine

| Dependent Variable | Geometric Mean[a] | | Ratio (%)[b] (Test/Ref) | 90% CI[c] | | ANOVA | |
|---|---|---|---|---|---|---|---|
| | Test | Ref | | Lower | Upper | Power | CV % |
| $\ln(C_{max})$ | 5431.5970 | 5657.0376 | 96.01 | 88.29 | 104.42 | 0.9961 | 23.69 |
| $\ln(AUC_{last})$ | 45456.8371 | 52788.4107 | 86.11 | 80.44 | 92.18 | 0.9998 | 19.14 |
| $\ln(AUC_{inf})$ | 47445.5869 | 55696.4070 | 85.19 | 79.64 | 91.12 | 0.9998 | 18.91 |

[a]Geometric Mean for the Test Product (Test) and Reference Product (Ref) based on Least Squares Mean of log-transformed parameter values
[b]Ratio(%) = Geometric Mean (Test)/Geometric Mean (Ref)
[c]90% Confidence Interval

TABLE 60

Statistical Analysis of the Log-Transformed Systemic Exposure Parameters of Norbuprenorphine

| Dependent Variable | Geometric Mean[a] | | Ratio (%)[b] (Test/Ref) | 90% CI[c] | | ANOVA | |
|---|---|---|---|---|---|---|---|
| | Test | Ref | | Lower | Upper | Power | CV % |
| $\ln(C_{max})$ | 703.1707 | 1772.8716 | 39.66 | 36.36 | 43.27 | 0.9941 | 24.60 |
| $\ln(AUC_{last})$ | 33655.6801 | 68872.0707 | 48.87 | 45.97 | 51.94 | 1.0000 | 17.14 |
| $\ln(AUC_{inf})$ | 40581.0836 | 81427.3060 | 49.84 | 46.26 | 53.70 | 0.9991 | 21.01 |

[a]Geometric Mean for the Test Product (Test) and Reference Product (Ref) based on Least Squares Mean of log-transformed parameter values
[b]Ratio(%) = Geometric Mean (Test)/Geometric Mean (Ref)
[c]90% Confidence Interval

TABLE 61

Statistical Analysis of the Log-Transformed Systemic Exposure Parameters of Unconjugated Naloxone

| Dependent Variable | Geometric Mean[a] Test | Ref | Ratio (%)[b] (Test/Ref) | 90% CI[c] Lower | Upper | ANOVA Power | CV % |
|---|---|---|---|---|---|---|---|
| ln($C_{max}$) | 339.8783 | 327.6977 | 103.72 | 93.78 | 114.71 | 0.9764 | 28.62 |
| ln($AUC_{last}$) | 824.7608 | 868.5854 | 94.95 | 86.93 | 103.72 | 0.9931 | 24.96 |
| ln($AUC_{inf}$) | 828.9973 | 875.5051 | 94.69 | 86.79 | 103.31 | 0.9940 | 24.64 |

[a] Geometric Mean for the Test Product (Test) and Reference Product (Ref) based on Least Squares Mean of log-transformed parameter values
[b] Ratio(%) = Geometric Mean (Test)/Geometric Mean (Ref)
[c] 90% Confidence Interval

TABLE 62

Statistical Analysis of the Log-Transformed Systemic Exposure Parameters of Total Naloxone

| Dependent Variable | Geometric Mean[a] Test | Ref | Ratio (%)[b] (Test/Ref) | 90% CI[c] Lower | Upper | ANOVA Power | CV % |
|---|---|---|---|---|---|---|---|
| ln($C_{max}$) | 9.5951 | 20.9370 | 45.83 | 39.77 | 52.82 | 0.8295 | 41.12 |
| ln($AUC_{last}$) | 30.8413 | 60.7760 | 50.75 | 47.16 | 54.60 | 0.9993 | 20.61 |
| ln($AUC_{inf}$) | 32.8603 | 62.0280 | 52.98 | 49.53 | 56.67 | 0.9998 | 18.47 |

[a] Geometric Mean for the Test Product (Test) and Reference Product (Ref) based on Least Squares Mean of log-transformed parameter values
[b] Ratio(%) = Geometric Mean (Test)/Geometric Mean (Ref)
[c] 90% Confidence Interval

TABLE 63

Statistical Analysis of the Log-Transformed Partial AUCs of Buprenorphine

| Dependent Variable | Geometric Mean[a] Test | Ref | Ratio (%)[b] (Test/Ref) | 90% CI[c] Lower | Upper | ANOVA Power | CV % |
|---|---|---|---|---|---|---|---|
| ln($AUC_{0-72}$) | 42137.3401 | 47665.3869 | 88.40 | 82.59 | 94.62 | 0.9998 | 19.12 |
| ln($AUC_{0-96}$) | 43841.7217 | 50179.2267 | 87.37 | 81.68 | 93.46 | 0.9998 | 18.93 |
| ln($AUC_{0-120}$) | 44970.3912 | 51838.9927 | 86.75 | 81.12 | 92.77 | 0.9998 | 18.84 |
| ln($AUC_{0-144}$) | 45740.0908 | 52993.1994 | 86.31 | 80.72 | 92.29 | 0.9998 | 18.82 |

[a] Geometric Mean for the Test Product (Test) and Reference Product (Ref) based on Least Squares Mean of log-transformed parameter values
[b] Ratio(%) = Geometric Mean (Test)/Geometric Mean (Ref)
[c] 90% Confidence Interval

TABLE 64

Statistical Analysis of the Log-Transformed Partial AUCs of Unconjugated Naloxone

| Dependent Variable | Geometric Mean[a] Test | Ref | Ratio (%)[b] (Test/Ref) | 90% CI[c] Lower | Upper | ANOVA Power | CV % |
|---|---|---|---|---|---|---|---|
| ln($AUC_{0-72}$) | 827.2680 | 874.7880 | 94.57 | 86.67 | 103.18 | 0.9939 | 24.66 |
| ln($AUC_{0-96}$) | 827.9833 | 875.1413 | 94.61 | 86.71 | 103.23 | 0.9939 | 24.66 |
| ln($AUC_{0-120}$) | 828.3676 | 875.2500 | 94.64 | 86.74 | 103.27 | 0.9939 | 24.65 |
| ln($AUC_{0-144}$) | 828.5919 | 875.2984 | 94.66 | 86.76 | 103.29 | 0.9940 | 24.65 |

[a] Geometric Mean for the Test Product (Test) and Reference Product (Ref) based on Least Squares Mean of log-transformed parameter values
[b] Ratio(%) = Geometric Mean (Test)/Geometric Mean (Ref)
[c] 90% Confidence Interval Example 10: Pharmacokinetic Data for Formulation 21

Objective

The primary objective of this study was to compare the bioavailability of a test formulation of Buprenorphine-Naloxone Sublingual (SL) spray, 2.2 mg/0.55 mg (1 spray) to that of a single dose of Suboxone (buprenorphine and naloxone) sublingual film, 4 mg/1 mg, under fasted conditions. The secondary objective was to evaluate the safety and tolerability of Buprenorphine-Naloxone SL spray.

Study Design

This was a single-dose, open-label, randomized, two-period, two-treatment crossover study. Fifty-six healthy subjects were enrolled. Subjects who successfully completed the screening process checked into the research center the evening before first dose. Subjects who continued to meet inclusion/exclusion criteria the morning of dose were assigned a subject number, based on the order in which they successfully completed the screening process and procedures as outlined in the study protocol. Subjects were randomly assigned to a treatment sequence and received two separate single-dose administrations of study medication, one treatment per period, according to the randomization schedule. Dosing days were separated by a washout period of at least 14 days.

Subjects received each of the treatments listed below during the two treatment periods:
Treatment A: Test Product
Buprenorphine Naloxone SL spray, 2.2 mg/0.55 mg
Dose=1 sublingual spray (total dose 2.2 mg/0.55 mg)
Treatment B: Reference Product
Suboxone® (buprenorphine and naloxone) sublingual film, 4 mg/1 mg
Dose=1×4 mg/1 mg sublingual film
Clinical Procedures Summary During each study period, 6 mL blood samples were obtained for buprenorphine, norbuprenorphine, and unconjugated naloxone analysis before and after each dose at selected times through 168 hours after dose administration. A total of 36 pharmacokinetic (PK) blood samples were collected from each subject for buprenorphine, norbuprenorphine, and unconjugated naloxone, 18 samples in each study period. In addition, 6 mL blood samples were obtained for total naloxone analysis before and after each dose at selected times through 72 hours after dose administration. A total of 28 PK blood samples were collected from each subject for naloxone analysis, 14 samples in each study period.
Procedures for Collecting Samples for Pharmacokinetic Analysis Blood samples (1×6 mL) for buprenorphine, norbuprenorphine, and unconjugated naloxone analysis were collected at 0 (predose), and at 5 minutes, 10 minutes, 15 minutes, 30 minutes, and 1, 2, 4, 8, 12, 24, 36, 48, 72, 96, 120, 144, and 168 hours post dose (18 time points).

Blood samples (1×6 mL) for total naloxone analysis were collected in Vacutainer tubes containing $K_2$-EDTA as a preservative at 0 (predose), and at 5 minutes, 10 minutes, 15 minutes, 30 minutes, and 1, 2, 4, 8, 12, 24, 36, 48, and 72 hours (14 time points).
Bioanalytical Summary Plasma samples were analyzed for buprenorphine, norbuprenorphine, unconjugated naloxone, and total naloxone by Worldwide Clinical Trials (WCT) using validated LC-MS-MS procedures. The methods were validated for ranges of 20.0 to 10,000 pg/mL for buprenorphine and norbuprenorphine and 2.00 to 1000 pg/mL for unconjugated naloxone, based on the analysis of 1.00 mL of human EDTA plasma, and 0.0500 to 50.0 ng/mL for total naloxone, based on the analysis of 0.200 mL of human EDTA plasma. Data were stored in Watson Laboratory Information Management System (LIMS; Version 7.2.0.03, Thermo Fisher Scientific). Details of the method validation and sample analysis procedure are provided in the Method Validation Report and Bioanalytical Report sections.
Pharmacokinetic Analysis Concentration-time data were analyzed using noncompartmental methods in Phoenix™ WinNonlin® (Version 6.3, Pharsight Corporation). Concentration-time data that were below the limit of quantification (BLQ) were treated as zero in the data summarization and descriptive statistics. In the pharmacokinetic analysis, BLQ concentrations were treated as zero.

The following pharmacokinetic parameters were calculated: peak concentration in plasma ($C_{max}$), time to peak concentration ($T_{max}$), elimination rate constant ($\lambda_z$), terminal half-life ($T_{1/2}$), area under the concentration-time curve from time-zero to the time of the last quantifiable concentration ($AUC_{last}$), area under the plasma concentration time curve from time-zero extrapolated to infinity ($AUC_{inf}$).

Analysis of variance (ANOVA) and the Schuirmann's two one-sided t-test procedure at the 5% significance level were applied to the log-transformed pharmacokinetic exposure parameters, $C_{max}$, $AUC_{last}$, and $AUC_{inf}$. The 90% confidence interval for the ratio of the geometric means (Test/Reference) was calculated. Bioequivalence was declared if the lower and upper confidence intervals of the log-transformed parameters were within 80% to 125%.
Results.

Data from 52 subjects who completed at least one study period were included in the pharmacokinetic analysis. Data from 50 subjects who completed both study periods were included in the statistical analysis. Mean concentration-time data are shown in Tables 65 through 68. Results of the pharmacokinetic and statistical analyses are shown below in Tables 69 through 76.
Conclusions Buprenorphine exposure, based on $\ln(AUC_{last})$ and $\ln(AUC_{inf})$, was comparable across treatments and the 90% confidence intervals were within the accepted of 80% to 125% limits for demonstrating similar bioavailability between Buprenorphine Naloxone SL spray, 2.2 mg/0.55 mg and Suboxone sublingual film, 4 mg/1 mg. Buprenorphine $C_{max}$ was approximately 27% higher after the administration of Buprenorphine Naloxone SL spray, 2.2 mg/0.55 mg compared to that after Suboxone sublingual film, 4 mg/1 mg.

Peak and overall systemic exposure to unconjugated naloxone, based on $\ln(C_{max})$, $\ln(AUC_{last})$, and $\ln(AUC_{inf})$, was approximately 31 to 66% higher after the administration of Buprenorphine Naloxone SL spray, 2.2 mg/0.55 mg compared to that after Suboxone sublingual film, 4 mg/1 mg.

TABLE 65

Buprenorphine Concentration-Time Data after Administration of the Test Product (Treatment A) and the Reference Product (Treatment B).

| | | Treatment A: Test Product | | | Treatment B: Reference Product (Suboxone) | | |
|---|---|---|---|---|---|---|---|
| Time (h) | n | Mean (pg/mL) | SD (pg/mL) | CV (%) | n | Mean (pg/mL) | SD (pg/mL) | CV (%) |
| 0.00 | 50 | 0.00 | 0.00 | NC | 52 | 0.00 | 0.00 | NC |
| 0.08 | 50 | 12.9 | 42.7 | 330.40 | 52 | 0.00 | 0.00 | NC |
| 0.17 | 50 | 170 | 172 | 101.40 | 51 | 5.02 | 12.4 | 246.05 |
| 0.25 | 50 | 514 | 453 | 88.26 | 52 | 69.4 | 90.8 | 130.89 |

TABLE 65-continued

Buprenorphine Concentration-Time Data after Administration of the Test Product (Treatment A) and the Reference Product (Treatment B).

| | | Treatment A: Test Product | | | | Treatment B: Reference Product (Suboxone) | | |
|---|---|---|---|---|---|---|---|---|
| Time (h) | n | Mean (pg/mL) | SD (pg/mL) | CV (%) | n | Mean (pg/mL) | SD (pg/mL) | CV (%) |
| 0.50 | 50 | 1360 | 809 | 59.36 | 52 | 655 | 455 | 69.47 |
| 1.00 | 50 | 2140 | 953 | 44.44 | 52 | 1470 | 633 | 43.22 |
| 2.00 | 50 | 2320 | 850 | 36.58 | 52 | 1930 | 730 | 37.89 |
| 4.00 | 50 | 1530 | 546 | 35.60 | 52 | 1310 | 539 | 41.13 |
| 8.00 | 50 | 498 | 196 | 39.33 | 52 | 494 | 191 | 38.56 |
| 12.00 | 50 | 241 | 85.0 | 35.28 | 52 | 281 | 112 | 39.66 |
| 24.00 | 50 | 120 | 45.9 | 38.13 | 52 | 158 | 66.5 | 42.21 |
| 36.00 | 49 | 80.5 | 25.4 | 31.57 | 52 | 107 | 34.6 | 32.36 |
| 48.00 | 49 | 59.8 | 19.5 | 32.53 | 52 | 76.5 | 25.5 | 33.27 |
| 72.00 | 49 | 31.7 | 15.7 | 49.54 | 52 | 45.0 | 18.5 | 41.08 |
| 96.00 | 49 | 18.1 | 15.4 | 85.22 | 52 | 27.1 | 18.1 | 66.82 |
| 120.00 | 49 | 4.48 | 10.7 | 239.47 | 52 | 12.3 | 15.4 | 125.50 |
| 144.00 | 49 | 2.19 | 7.60 | 347.35 | 52 | 4.58 | 10.5 | 229.39 |
| 168.00 | 49 | 0.580 | 4.06 | 700.00 | 52 | 1.45 | 6.10 | 420.91 |

Note:
Plasma samples analyzed using a bioanalytical method with a validated range 20.0 to 10,000 pg/mL; concentrations reported in pg/mL to 3 significant figures; concentrations below limit of quantification set to zero (0.00 pg/mL) in the data summarization
NC = Not calculated

TABLE 66

Norbuprenorphine Concentration-Time Data after Administration of the Test Product (Treatment A) and the Reference Product (Treatment B).

| | | Treatment A: Test Product | | | | Treatment B: Reference Product (Suboxone) | | |
|---|---|---|---|---|---|---|---|---|
| Time (h) | n | Mean (pg/mL) | SD (pg/mL) | CV (%) | n | Mean (pg/mL) | SD (pg/mL) | CV (%) |
| 0.00 | 50 | 0.00 | 0.00 | NC | 52 | 0.00 | 0.00 | NC |
| 0.08 | 50 | 0.00 | 0.00 | NC | 52 | 0.00 | 0.00 | NC |
| 0.17 | 50 | 4.87 | 22.6 | 463.38 | 51 | 0.613 | 4.38 | 714.14 |
| 0.25 | 50 | 33.2 | 70.6 | 212.49 | 52 | 14.4 | 39.1 | 272.22 |
| 0.50 | 50 | 119 | 149 | 124.82 | 52 | 271 | 393 | 145.18 |
| 1.00 | 50 | 193 | 155 | 80.49 | 52 | 432 | 329 | 76.08 |
| 2.00 | 50 | 217 | 117 | 53.83 | 52 | 461 | 252 | 54.53 |
| 4.00 | 50 | 196 | 89.5 | 45.56 | 52 | 364 | 168 | 46.04 |
| 8.00 | 50 | 179 | 92.1 | 51.45 | 52 | 328 | 167 | 50.84 |
| 12.00 | 50 | 164 | 83.1 | 50.69 | 52 | 305 | 159 | 52.06 |
| 24.00 | 50 | 155 | 74.4 | 48.14 | 52 | 294 | 142 | 48.10 |
| 36.00 | 49 | 130 | 56.8 | 43.66 | 52 | 237 | 97.8 | 41.33 |
| 48.00 | 49 | 106 | 44.8 | 42.23 | 52 | 188 | 79.6 | 42.44 |
| 72.00 | 49 | 70.8 | 30.5 | 43.05 | 52 | 127 | 49.7 | 39.26 |
| 96.00 | 49 | 51.5 | 28.4 | 55.22 | 52 | 90.6 | 44.6 | 49.20 |
| 120.00 | 49 | 30.6 | 24.4 | 79.65 | 52 | 58.5 | 29.6 | 50.58 |
| 144.00 | 49 | 21.2 | 22.5 | 106.17 | 52 | 39.2 | 28.7 | 73.24 |
| 168.00 | 49 | 16.2 | 20.8 | 127.83 | 52 | 29.5 | 28.0 | 94.98 |

Note:
Plasma samples analyzed using a bioanalytical method with a validated range 20.0 to 10,000 pg/mL; concentrations reported in pg/mL to 3 significant figures; concentrations below limit of quantification set to zero (0.00 pg/mL) in the data summarization
NC = Not calculated

TABLE 67

Unconjugated Naloxone Concentration-Time Data after Administration of the Test Product (Treatment A) and the Reference Product (Treatment B).

| | | Treatment A: Test Product | | | | Treatment B: Reference Product (Suboxone) | | |
|---|---|---|---|---|---|---|---|---|
| Time (h) | n | Mean (pg/mL) | SD (pg/mL) | CV (%) | n | Mean (pg/mL) | SD (pg/mL) | CV (%) |
| 0.00 | 50 | 0.00 | 0.00 | NC | 52 | 0.00 | 0.00 | NC |
| 0.08 | 50 | 22.6 | 28.7 | 127.14 | 52 | 0.141 | 0.710 | 505.16 |

TABLE 67-continued

Unconjugated Naloxone Concentration-Time Data after Administration of the Test Product (Treatment A) and the Reference Product (Treatment B).

| | | Treatment A: Test Product | | | | Treatment B: Reference Product (Suboxone) | | |
|---|---|---|---|---|---|---|---|---|
| Time (h) | n | Mean (pg/mL) | SD (pg/mL) | CV (%) | n | Mean (pg/mL) | SD (pg/mL) | CV (%) |
| 0.17 | 50 | 69.6 | 48.1 | 69.17 | 51 | 8.12 | 11.0 | 135.57 |
| 0.25 | 50 | 115 | 80.1 | 69.56 | 52 | 27.7 | 32.2 | 116.37 |
| 0.50 | 50 | 140 | 71.9 | 51.43 | 52 | 75.1 | 49.2 | 65.49 |
| 1.00 | 50 | 112 | 50.5 | 44.89 | 52 | 82.3 | 37.7 | 45.84 |
| 2.00 | 50 | 65.3 | 34.4 | 52.62 | 52 | 52.4 | 20.4 | 38.88 |
| 4.00 | 50 | 21.8 | 14.7 | 67.22 | 52 | 18.4 | 10.1 | 54.68 |
| 8.00 | 50 | 3.01 | 2.55 | 84.83 | 52 | 4.09 | 3.42 | 83.71 |
| 12.00 | 50 | 0.480 | 1.23 | 257.25 | 52 | 1.46 | 2.43 | 166.08 |
| 24.00 | 50 | 0.0598 | 0.423 | 707.11 | 52 | 0.297 | 0.944 | 318.00 |
| 36.00 | 49 | 0.00 | 0.00 | NC | 52 | 0.00 | 0.00 | NC |
| 48.00 | 49 | 0.00 | 0.00 | NC | 52 | 0.00 | 0.00 | NC |
| 72.00 | 49 | 0.00 | 0.00 | NC | 52 | 0.00 | 0.00 | NC |
| 96.00 | 49 | 0.00 | 0.00 | NC | 52 | 0.00 | 0.00 | NC |
| 120.00 | 49 | 0.00 | 0.00 | NC | 52 | 0.00 | 0.00 | NC |
| 144.00 | 49 | 0.00 | 0.00 | NC | 52 | 0.00 | 0.00 | NC |
| 168.00 | 49 | 0.00 | 0.00 | NC | 52 | 0.00 | 0.00 | NC |

Note:
Plasma samples analyzed using a bioanalytical method with a validated range 2.00 to 1000 pg/mL; concentrations reported in pg/mL to 3 significant figures; concentrations below limit of quantification set to zero (0.00 pg/mL) in the data summarization
NC = Not calculated

TABLE 68

Total Naloxone Concentration-Time Data after Administration of the Test Product (Treatment A) and the Reference Product (Treatment B).

| | | Treatment A: Test Product | | | | Treatment B: Reference Product (Suboxone) | | |
|---|---|---|---|---|---|---|---|---|
| Time (h) | n | Mean (ng/mL) | SD (ng/mL) | CV (%) | n | Mean (ng/mL) | SD (ng/mL) | CV (%) |
| 0.00 | 50 | 0.00 | 0.00 | NC | 52 | 0.00 | 0.00 | NC |
| 0.08 | 50 | 0.0538 | 0.116 | 216.21 | 52 | 0.00453 | 0.0198 | 437.39 |
| 0.17 | 50 | 0.486 | 0.756 | 155.58 | 51 | 0.105 | 0.307 | 292.49 |
| 0.25 | 50 | 1.36 | 1.60 | 117.10 | 52 | 1.02 | 1.54 | 150.08 |
| 0.50 | 50 | 2.69 | 2.32 | 86.33 | 52 | 7.95 | 6.80 | 85.51 |
| 1.00 | 50 | 3.22 | 2.34 | 72.61 | 52 | 6.28 | 3.58 | 57.03 |
| 2.00 | 50 | 1.74 | 0.983 | 56.49 | 52 | 3.50 | 1.71 | 48.75 |
| 4.00 | 50 | 0.658 | 0.468 | 71.21 | 52 | 1.21 | 0.902 | 74.26 |
| 8.00 | 50 | 0.321 | 0.146 | 45.65 | 52 | 0.570 | 0.290 | 50.96 |
| 12.00 | 50 | 0.198 | 0.0980 | 49.49 | 52 | 0.372 | 0.187 | 50.21 |
| 24.00 | 50 | 0.0679 | 0.0496 | 73.01 | 52 | 0.124 | 0.0642 | 51.62 |
| 36.00 | 49 | 0.00129 | 0.00904 | 700.00 | 52 | 0.0116 | 0.0304 | 261.88 |
| 48.00 | 49 | 0.00 | 0.00 | NC | 52 | 0.00 | 0.00 | NC |
| 72.00 | 49 | 0.00 | 0.00 | NC | 52 | 0.00 | 0.00 | NC |

Note:
Plasma samples analyzed using a bioanalytical method with a validated range 0.0500 to 50.0 ng/mL; concentrations reported in ng/mL to 3 significant figures; concentrations below limit of quantification set to zero (0.00 ng/mL) in the data summarization
NC = Not calculated

TABLE 69

Pharmacokinetic Parameters of Buprenorphine

| | | Treatment A: Test Product | | | | Treatment B: Reference Product (Suboxone) | | |
|---|---|---|---|---|---|---|---|---|
| Parameter | n | Mean | SD | CV % | n | Mean | SD | CV % |
| $T_{max}$ (h) | 50 | 1.68 | 0.73 | 43.26 | 52 | 1.98 | 0.72 | 36.38 |
| $C_{max}$ (pg/mL) | 50 | 2470 | 850 | 34.35 | 52 | 1990 | 703 | 35.43 |
| $AUC_{last}$ (h*pg/mL) | 50 | 18010 | 6118 | 33.97 | 52 | 18240 | 5820 | 31.91 |
| $AUC_{inf}$ (h*pg/mL) | 50 | 19320 | 6190 | 32.04 | 52 | 19590 | 6018 | 30.72 |
| $AUC_{Extrap}$ (%) | 50 | 7.39 | 3.84 | 51.88 | 52 | 7.23 | 2.65 | 36.72 |
| $\lambda_z$ (h$^{-1}$) | 50 | 0.0244 | 0.0130 | 53.20 | 52 | 0.0217 | 0.0078 | 35.71 |

TABLE 69-continued

Pharmacokinetic Parameters of Buprenorphine

| Parameter | Treatment A: Test Product | | | | Treatment B: Reference Product (Suboxone) | | | |
|---|---|---|---|---|---|---|---|---|
| | n | Mean | SD | CV % | n | Mean | SD | CV % |
| $T_{1/2}$ (h) | 50 | 33.99 | 14.07 | 41.40 | 52 | 35.59 | 11.28 | 31.69 |
| $T_{last}$ (h) | 50 | 89.28 | 27.87 | 31.22 | 52 | 105.23 | 28.97 | 27.53 |
| $C_{last}$ (pg/mL) | 50 | 28.2 | 11.0 | 38.96 | 52 | 26.4 | 5.98 | 22.65 |

Note:
Full precision data used in pharmacokinetic analysis

TABLE 70

Pharmacokinetic Parameters of Norbuprenorphine

| Parameter | Treatment A: Test Product | | | | Treatment B: Reference Product (Suboxone) | | | |
|---|---|---|---|---|---|---|---|---|
| | n | Mean | SD | CV % | n | Mean | SD | CV % |
| $T_{max}$ (h) | 50 | 5.54 | 8.06 | 145.49 | 52 | 4.00 | 5.62 | 140.60 |
| $C_{max}$ (pg/mL) | 50 | 265 | 162 | 61.11 | 52 | 566 | 350 | 61.76 |
| $AUC_{last}$ (h*pg/mL) | 50 | 12360 | 5387 | 43.57 | 52 | 23270 | 9030 | 38.80 |
| $AUC_{inf}$ (h*pg/mL) | 50 | 15370 | 6778 | 44.09 | 52 | 26980 | 11550 | 42.82 |
| $AUC_{Extrap}$ (%) | 50 | 19.24 | 12.97 | 67.42 | 52 | 12.48 | 11.68 | 93.57 |
| $\lambda_z (h^{-1})$ | 50 | 0.0165 | 0.0095 | 57.42 | 52 | 0.0168 | 0.0072 | 42.94 |
| $T_{1/2}$ (h) | 50 | 56.34 | 39.94 | 70.89 | 52 | 53.41 | 42.88 | 80.29 |
| $T_{last}$ (h) | 50 | 131.52 | 38.25 | 29.09 | 52 | 152.77 | 23.78 | 15.56 |
| $C_{last}$ (pg/mL) | 50 | 34.0 | 13.8 | 40.44 | 52 | 39.0 | 20.0 | 51.24 |

Note:
Full precision data used in pharmacokinetic analysis

TABLE 71

Pharmacokinetic Parameters of Unconjugated Naloxone

| Parameter | Treatment A: Test Product | | | | Treatment B: Reference Product (Suboxone) | | | |
|---|---|---|---|---|---|---|---|---|
| | n | Mean | SD | CV % | n | Mean | SD | CV % |
| $T_{max}$ (h) | 50 | 0.54 | 0.26 | 47.66 | 52 | 0.95 | 0.45 | 46.82 |
| $C_{max}$ (pg/mL) | 50 | 153 | 78.4 | 51.37 | 52 | 89.8 | 43.9 | 48.83 |
| $AUC_{last}$ (h*pg/mL) | 50 | 310.2 | 156.8 | 50.57 | 52 | 232.6 | 105.0 | 45.16 |
| $AUC_{inf}$ (h*pg/mL) | 50 | 320.6 | 158.3 | 49.37 | 44 | 262.0 | 110.1 | 42.04 |
| $AUC_{Extrap}$ (%) | 50 | 4.09 | 3.98 | 97.30 | 44 | 4.86 | 2.83 | 58.26 |
| $\lambda_z (h^{-1})$ | 50 | 0.4972 | 0.1191 | 23.95 | 44 | 0.3643 | 0.1447 | 39.72 |
| $T_{1/2}$ (h) | 50 | 1.58 | 1.06 | 67.25 | 44 | 2.60 | 2.28 | 87.94 |
| $T_{last}$ (h) | 50 | 7.92 | 3.38 | 42.67 | 52 | 10.15 | 5.16 | 50.83 |
| $C_{last}$ (pg/mL) | 50 | 5.28 | 4.51 | 85.35 | 52 | 4.16 | 2.52 | 60.67 |

Note:
Full precision data used in pharmacokinetic analysis

TABLE 72

Pharmacokinetic Parameters of Total Naloxone

| Parameter | Treatment A: Test Product | | | | Treatment B: Reference Product (Suboxone) | | | |
|---|---|---|---|---|---|---|---|---|
| | n | Mean | SD | CV % | n | Mean | SD | CV % |
| $T_{max}$ (h) | 50 | 1.17 | 1.26 | 108.00 | 52 | 1.02 | 0.70 | 68.67 |
| $C_{max}$ (ng/mL) | 50 | 4.26 | 2.52 | 59.05 | 52 | 9.95 | 5.47 | 54.92 |
| $AUC_{last}$ (h*ng/mL) | 50 | 10.68 | 3.908 | 36.60 | 52 | 21.34 | 6.554 | 30.72 |
| $AUC_{inf}$ (h*ng/mL) | 49 | 11.87 | 3.903 | 32.89 | 52 | 22.70 | 6.714 | 29.58 |
| $AUC_{Extrap}$ (%) | 49 | 9.54 | 7.78 | 81.57 | 52 | 6.24 | 3.59 | 57.52 |
| $\lambda_z (h^{-1})$ | 49 | 0.1161 | 0.0579 | 49.87 | 52 | 0.1066 | 0.0372 | 34.84 |
| $T_{1/2}$ (h) | 49 | 7.21 | 3.33 | 46.21 | 52 | 7.35 | 2.81 | 38.28 |

TABLE 72-continued

Pharmacokinetic Parameters of Total Naloxone

| Parameter | Treatment A: Test Product | | | | Treatment B: Reference Product (Suboxone) | | | |
|---|---|---|---|---|---|---|---|---|
| | n | Mean | SD | CV % | n | Mean | SD | CV % |
| $T_{last}$ (h) | 50 | 21.04 | 5.87 | 27.91 | 52 | 24.69 | 5.53 | 22.39 |
| $C_{last}$ (pg/mL) | 50 | 0.102 | 0.0428 | 42.00 | 52 | 0.136 | 0.104 | 76.93 |

Note:
Full precision data used in pharmacokinetic analysis

TABLE 73

Statistical Analysis of the Log-Transformed Systemic Exposure Parameters of Buprenorphine

| Dependent Variable | Geometric Mean[a] | | Ratio (%)[b] | 90% CI[c] | | ANOVA | |
|---|---|---|---|---|---|---|---|
| | Test | Ref | (Test/Ref) | Lower | Upper | Power | CV % |
| $\ln(C_{max})$ | 2334.8796 | 1842.7190 | 126.71 | 114.98 | 139.63 | 0.9827 | 29.55 |
| $\ln(AUC_{last})$ | 17009.6037 | 17098.2817 | 99.48 | 91.06 | 108.69 | 0.9930 | 26.82 |
| $\ln(AUC_{inf})$ | 18379.2372 | 18433.5928 | 99.71 | 91.61 | 108.52 | 0.9957 | 25.64 |

[a]Geometric Mean for the Test Product (Test) and Reference Product (Ref) based on Least Squares Mean of log-transformed parameter values
[b]Ratio(%) = Geometric Mean (Test)/Geometric Mean (Ref)
[c]90% Confidence Interval

TABLE 74

Statistical Analysis of the Log-Transformed Systemic Exposure Parameters of Norbuprenorphine

| Dependent Variable | Geometric Mean[a] | | Ratio (%)[b] | 90% CI[c] | | ANOVA | |
|---|---|---|---|---|---|---|---|
| | Test | Ref | (Test/Ref) | Lower | Upper | Power | CV % |
| $\ln(C_{max})$ | 228.7018 | 489.3838 | 46.73 | 43.28 | 50.47 | 0.9988 | 23.19 |
| $\ln(AUC_{last})$ | 11116.0926 | 21710.7037 | 51.20 | 47.09 | 55.67 | 0.9963 | 25.34 |
| $\ln(AUC_{inf})$ | 13986.5409 | 24965.8998 | 56.02 | 51.65 | 60.77 | 0.9974 | 24.59 |

[a]Geometric Mean for the Test Product (Test) and Reference Product (Ref) based on Least Squares Mean of log-transformed parameter values
[b]Ratio(%) = Geometric Mean (Test)/Geometric Mean (Ref)
[c]90% Confidence Interval

TABLE 75

Statistical Analysis of the Log-Transformed Systemic Exposure Parameters of Unconjugated Naloxone

| Dependent Variable | Geometric Mean[a] | | Ratio (%)[b] | 90% CI[c] | | ANOVA | |
|---|---|---|---|---|---|---|---|
| | Test | Ref | (Test/Ref) | Lower | Upper | Power | CV % |
| $\ln(C_{max})$ | 132.4558 | 79.8936 | 165.79 | 146.96 | 187.03 | 0.9200 | 37.10 |
| $\ln(AUC_{last})$ | 275.6491 | 210.1213 | 131.19 | 117.86 | 146.02 | 0.9622 | 32.75 |
| $\ln(AUC_{inf})$ | 287.6305 | 218.5298 | 131.62 | 118.45 | 146.26 | 0.9663 | 29.60 |

[a]Geometric Mean for the Test Product (Test) and Reference Product (Ref) based on Least Squares Mean of log-transformed parameter values
[b]Ratio(%) = Geometric Mean (Test)/Geometric Mean (Ref)
[c]90% Confidence Interval

TABLE 76

Statistical Analysis of the Log-Transformed
Systemic Exposure Parameters of Total Naloxone

| Dependent Variable | Geometric Mean[a] | | Ratio (%)[b] (Test/Ref) | 90% CI[c] | | ANOVA | |
|---|---|---|---|---|---|---|---|
| | Test | Ref | | Lower | Upper | Power | CV % |
| $\ln(C_{max})$ | 3.4477 | 8.5476 | 40.34 | 34.96 | 46.53 | 0.8245 | 44.57 |
| $\ln(AUC_{last})$ | 9.8049 | 20.6392 | 47.51 | 44.24 | 51.01 | 0.9996 | 21.45 |
| $\ln(AUC_{inf})$ | 11.1098 | 22.0499 | 50.39 | 47.23 | 53.75 | 0.9999 | 19.22 |

[a]Geometric Mean for the Test Product (Test) and Reference Product (Ref) based on Least Squares Mean of log-transformed parameter values
[b]Ratio(%) = Geometric Mean (Test)/Geometric Mean (Ref)
[c]90% Confidence Interval

What is claimed is:

1. A liquid formulation comprising an effective amount of buprenorphine, a pharmaceutically acceptable salt thereof, or a derivative thereof, water as a solvent, a mixture of an alcohol and a glycol as a cosolvent, and an antioxidant, wherein the ratio of antioxidant to buprenorphine is from 0.01:1 to 0.18:1.

2. The liquid formulation of claim 1 further comprising naloxone, a pharmaceutically acceptable salt thereof, or a derivative thereof.

3. The liquid formulation of claim 1, wherein the formulation is a liquid spray formulation.

4. The liquid formulation of claim 1, wherein the antioxidant is selected from the group consisting of butylated hydroxyanisole (BHA), butylated hydroxytoluene (BHT), methionine, sodium ascorbate, sodium thiosulfate, thioglycerol, cysteine hydrochloride monohydrate and a mixture thereof.

5. The liquid formulation of claim 1 wherein the formulation is a sublingual spray formulation and is capable of producing a droplet size distribution wherein greater than 98% of the composition particles are greater than 10 microns in diameter during administration.

6. The liquid formulation of claim 1 wherein the formulation is a sublingual spray formulation and is capable of producing a droplet size distribution wherein:
the mean Dv(10) is from about 10 to about 40 microns during administration;
the mean Dv(50) is from about 30 to about 80 microns during administration; and
the mean Dv(90) is from about 80 to about 200 microns during administration.

7. The liquid formulation of claim 1 wherein the formulation is a sublingual spray formulation and is capable of producing a spray plume that has an ovality ratio of from about 1.1 to 2.4.

8. The liquid formulation of claim 1 wherein the formulation is capable of producing a spray plume width that is from about 25 to about 45 millimeters during administration and a spray plume angle that is from about 30 to about 55 degrees during administration.

9. The liquid formulation of claim 1 that is capable of producing a D(4,3) of 50 to 95 microns.

10. The liquid formulation of claim 1 wherein the formulation is a sublingual spray formulation that is capable of producing a droplet size distribution wherein the $C_{max}$ (ng/mL) of buprenorphine is from about 0.6 to about 1.5.

11. The liquid formulation of claim 1 wherein the formulation is a sublingual spray formulation that is capable of producing a droplet size distribution wherein the $T_{max}$ of buprenorphine is from about 1.5 to about 1.9 hours following administration.

12. A sublingual spray formulation comprising:
buprenorphine, a pharmaceutically acceptable salt thereof or a derivative thereof;
water as a solvent in an amount from about 10% to about 95% w/w;
a cosolvent consisting of a mixture of an alcohol from about 10% w/w to about 80% w/w and a glycol in an amount from about 0.5% to about 50% w/w; and
an antioxidant,
wherein the ratio of antioxidant to buprenorphine is from 0.01:1 to 0.18:1 and the % w/w is weight by total weight of the formulation.

13. The formulation of claim 12 further comprising menthol from about 0.005% w/w to about 0.5% w/w.

14. The formulation of claim 13, wherein:
water as a solvent is at an amount from about 20% to about 60% w/w;
the cosolvent consists of a mixture of an alcohol from about 30% w/w to about 60% w/w and a glycol in an amount from about 1% to about 10% w/w; and.

15. The formulation of claim 13, wherein:
water as a solvent is at an amount from about 38% to about 40% w/w;
the cosolvent consists of a mixture of ethanol in an amount of 55% w/w and propylene glycol in an amount of about 5% w/w;
the antioxidant consists of a mixture of butylated hydroxyanisole (BHA) and butylated hydroxytoluene (BHT); and
menthol is at an amount of about 0.05% w/w.

16. A sublingual spray formulation comprising:
buprenorphine, a pharmaceutically acceptable salt thereof or a derivative thereof;
naloxone, a pharmaceutically acceptable salt thereof or a derivative thereof;
water;
a cosolvent consisting of a mixture of an alcohol and a glycol;
an antioxidant; and
a chelating agent,
wherein the ratio of antioxidant to buprenorphine is from 0.002:1 to 0.03:1.

17. The sublingual spray formulation of claim 16, wherein:
naloxone, a pharmaceutically acceptable salt thereof or a derivative thereof at an amount from about 0.1% to about 3% w/w;
water as a solvent in an amount from about 20% to about 45% w/w;
the cosolvent consists of a mixture of ethanol in an amount of 50% w/w to about 60% w/w and propylene glycol in an amount of about 4% w/w to 6% w/w;

the antioxidant is sodium ascorbate;

the chelating agent is disodium edetate at an amount of about 0.001% to about 0.01% w/w; and menthol is at an amount of about 0.005% to 0.5% w/w, wherein the % w/w is weight by total weight of the formulation.

18. The liquid formulation of claim 16, wherein the formulation is a sublingual spray formulation comprising:

naloxone, a pharmaceutically acceptable salt thereof or a derivative thereof at an amount from about 0.1% to about 3% w/w;

menthol at an amount of about 0.05% w/w;

disodium edetate at an amount of about 0.005% w/w;

sodium ascorbate ethanol in an amount of about 55%;

propylene glycol in an amount from about 5% w/w;

water in an amount from about 25% w/w to 40% w/w;

wherein the % w/w is weight by total weight of the formulation.

19. A method of treating pain comprising administering the liquid formulation of claim 16 to a patient in need thereof.

20. A method of treating opioid dependence comprising administering the liquid formulation of claim 2 to a patient in need thereof.

* * * * *